United States Patent
Longest et al.

(10) Patent No.: US 8,479,728 B2
(45) Date of Patent: Jul. 9, 2013

(54) EFFECTIVE DELIVERY OF NANOPARTICLES AND MICROMETER-SIZED PHARMACEUTICAL AEROSOLS TO THE LUNG THROUGH ENHANCED CONDENSATIONAL GROWTH

(75) Inventors: Philip Worth Longest, Richmond, VA (US); Jinxiang Xi, Little Rock, AR (US); Michael Hindle, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 276 days.

(21) Appl. No.: 12/866,869

(22) PCT Filed: Feb. 18, 2009

(86) PCT No.: PCT/US2009/034360
§ 371 (c)(1),
(2), (4) Date: Nov. 19, 2010

(87) PCT Pub. No.: WO2009/105445
PCT Pub. Date: Aug. 27, 2009

(65) Prior Publication Data
US 2011/0056492 A1    Mar. 10, 2011

(51) Int. Cl.
*A61M 16/10* (2006.01)
*A61M 15/00* (2006.01)
*A61M 16/00* (2006.01)
*F23D 11/00* (2006.01)
*F23D 14/02* (2006.01)

(52) U.S. Cl.
USPC .................................. 128/203.16; 128/203.26

(58) Field of Classification Search
USPC ............. 128/200.24, 203.12, 203.15–203.17, 128/203.26, 203.27, 204.17
See application file for complete search history.

(56) References Cited

U.S. PATENT DOCUMENTS

| | | | |
|---|---|---|---|
| 5,522,385 | A | 6/1996 | Lloyd et al. |
| 5,906,202 | A | 5/1999 | Schuster et al. |
| 2006/0147520 | A1 | 7/2006 | Ruegg |

FOREIGN PATENT DOCUMENTS

| | | |
|---|---|---|
| WO | WO 97/18003 | 5/1997 |
| WO | WO 02/55057 | 7/2002 |
| WO | WO 2007/041339 | 4/2007 |

*Primary Examiner* — Kristen Matter
(74) *Attorney, Agent, or Firm* — Whitham Curtis Christofferson & Cook, PC

(57) ABSTRACT

Methods and devices for inhalation therapy to deliver and embed (deposit) particles less than about 1 µm in diameter in the lung. High humidity treatment of the lungs causes condensational growth in particle size upon entering the lungs. Increased particle size is conducive to particle embedment (deposition) in deep lung tissue or at a specific targeted lung region.

17 Claims, 14 Drawing Sheets

Figure 2A

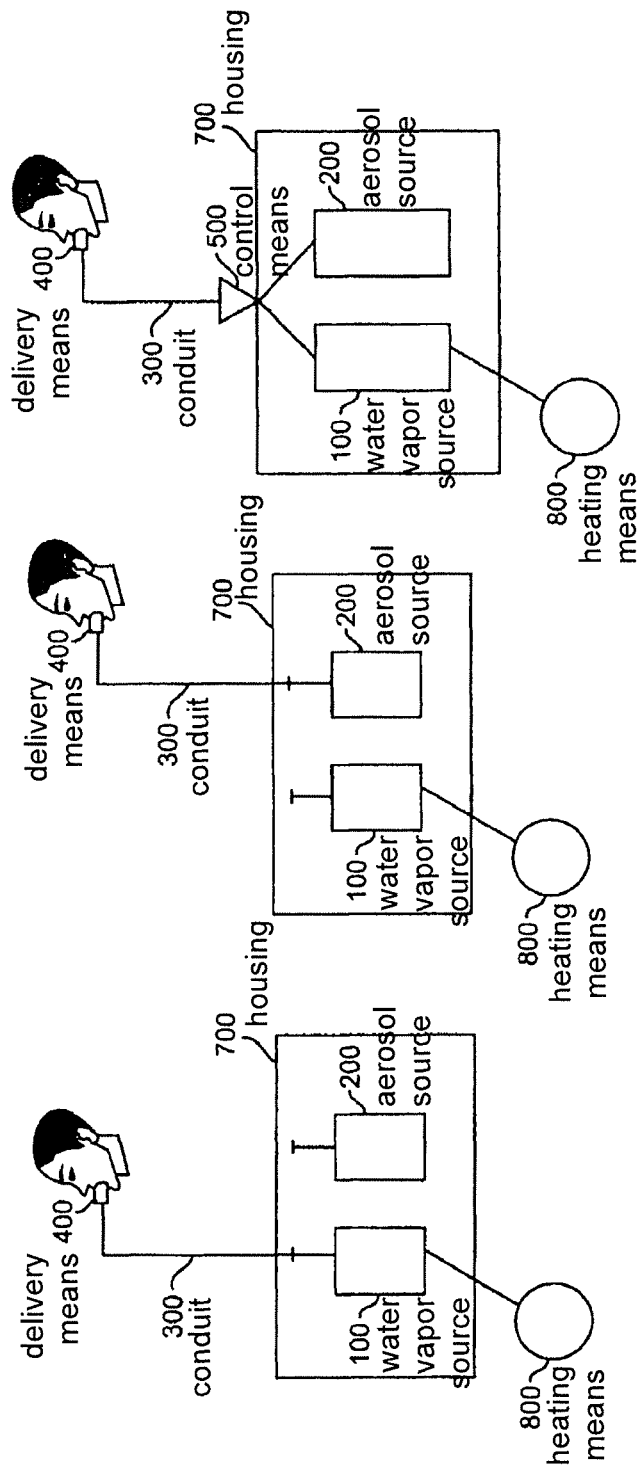

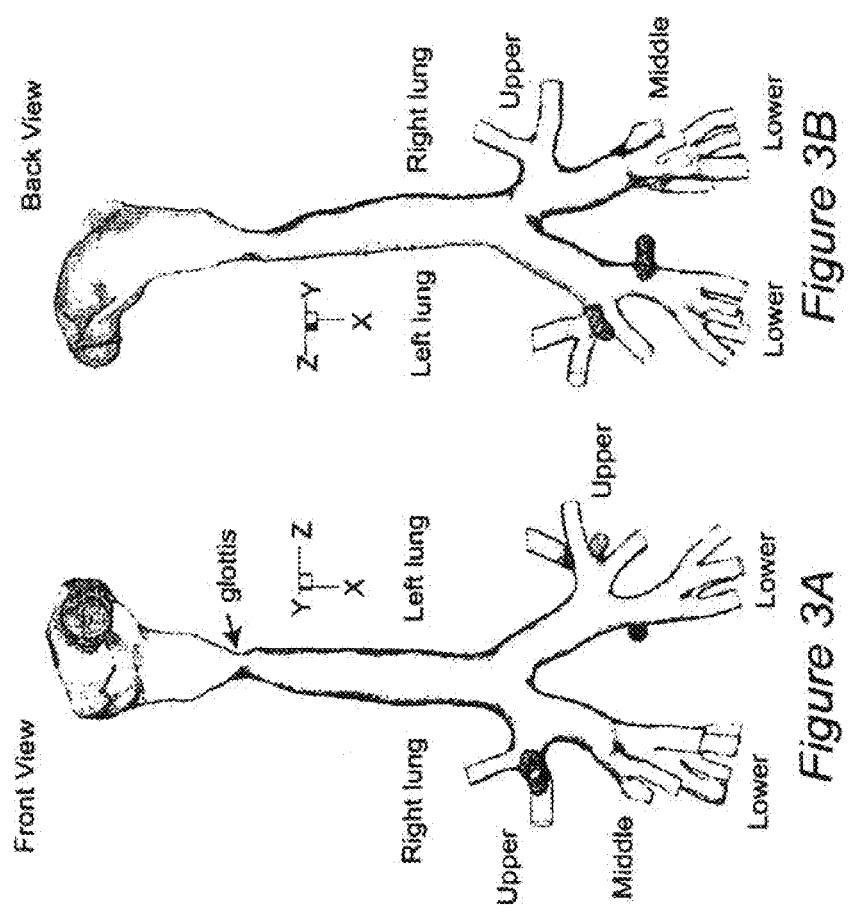

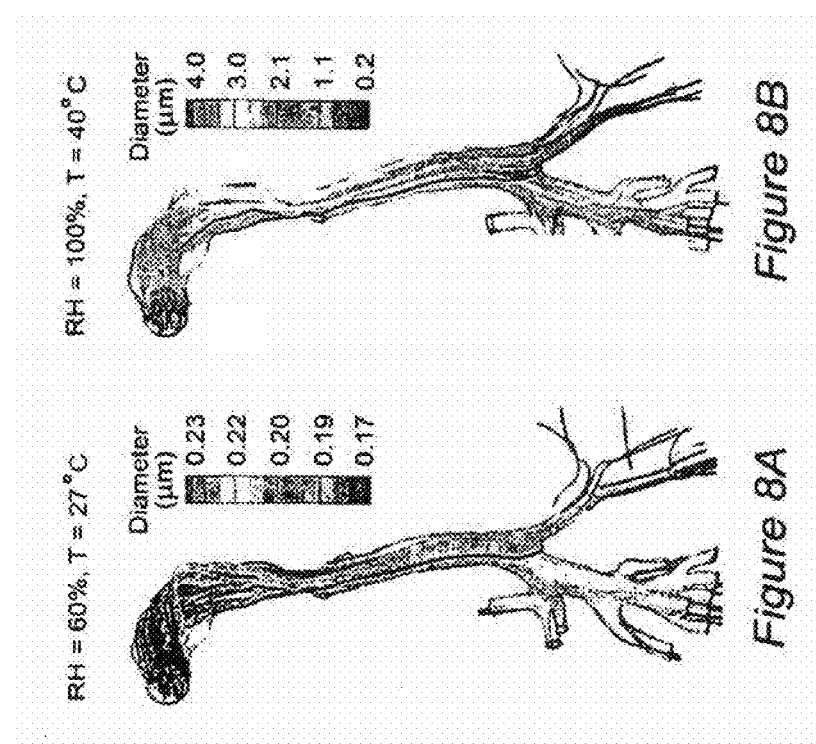

Figure 9

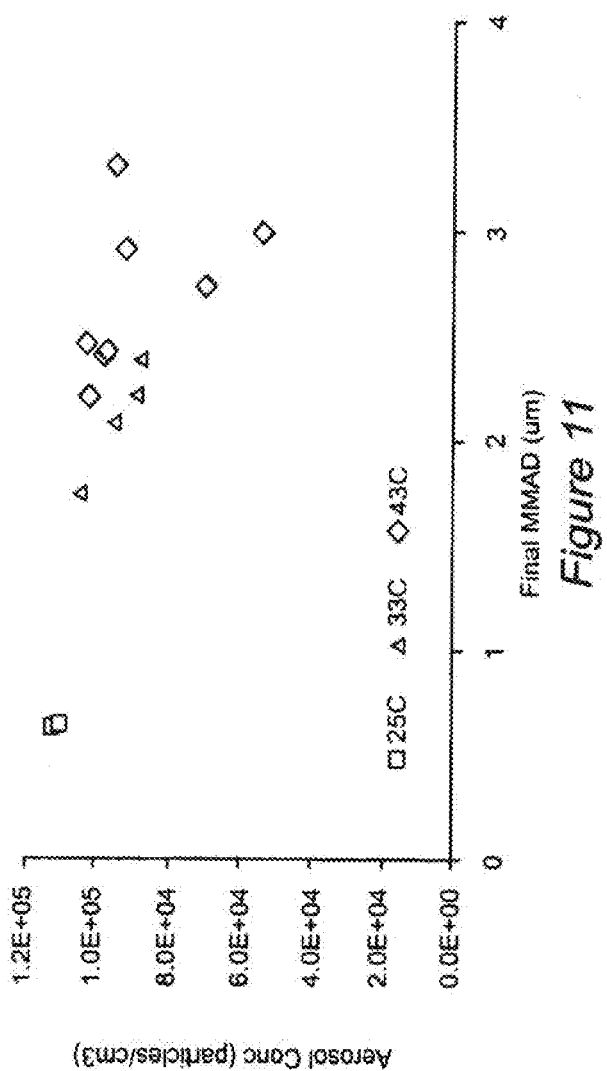

EFFECTIVE DELIVERY OF NANOPARTICLES AND MICROMETER-SIZED PHARMACEUTICAL AEROSOLS TO THE LUNG THROUGH ENHANCED CONDENSATIONAL GROWTH

CROSS-REFERENCE TO RELATED APPLICATIONS

This application is a 371 of international application PCT/US2009/034360 filed Feb. 11, 2009, which claims priority to U.S. Provisional Application 61/029,528 filed Feb. 18, 2008.

BACKGROUND OF THE INVENTION

1. Field of the Invention

The invention generally relates to inhalation therapy. In particular, the invention provides methods and devices to successfully deliver and embed (deposit) in the lungs particles less than about 1 μm in diameter, by increasing and controlling the humidity of the respiratory tract.

2. Background of the Invention

Inhaled pharmaceutical aerosols are often deposited in the lungs at very low deposition efficiencies. Perhaps more significant than the quantity of drug deposited is the large inter- and intra-subject variability that is often observed with these medicinal aerosols and the associated dose delivered to the lungs. For commonly used pressurized metered dose inhalers (pMDIs), variability in lung deposition can exceed 100% (Borgstrom et al., 2006). High variability in drug deposition typically requires an increase in dose to establish consistent long-term drug effectiveness. Increasing the dosage may be acceptable for traditional inhaled medications with relatively flat dose-response curves and low systemic side effects, such as current asthma therapies. In contrast, next generation locally and systemically acting inhaled medications are expected to have narrower effective therapeutic ranges, increased side effects, and will be more expensive. For some medications, the lungs provide an advantageous delivery route based on reduced metabolism and drug degradation, adequate bioavailability, rapid onset, and needle free administration. Inhaled insulin is a primary example of a systemically acting medication with a relatively narrow therapeutic range. In order to make many next generation inhaled medications viable drug delivery alternatives, decreased inter- and intra-subject variability is of critical importance (Byron 2004).

In order to effectively deliver inhaled respiratory aerosols into the lungs, deposition in the mouth, throat and upper bronchi should be avoided. Current pulmonary delivery devices often try to minimize deposition in the mouth-throat and upper bronchi by administering particles with diameters of approximately 4 μm or less and inhaling in a prescribed manner. It has been shown that 4 μm particles have low mouth-throat and tracheobronchial deposition with a maximum pulmonary (or deep lung) deposition (Martonen 1993). Controlled inhalation waveforms can also minimize mouth-throat deposition and maximize pulmonary (or deep lung) deposition through sedimentation (Smaldone 2006). However, deposition in the mouth-throat and upper tracheobronchial region remains significant, even for current state-of-the-art aerosol delivery devices (Dalby et al., 2004; Longest et al. 2007). Perhaps more importantly, deposition in the mouth-throat (MT) is highly variable (Borgstrom et al. 2006). As a result, the dose delivered to the lungs of individual patients can vary significantly, and the exact dose received is not known.

In order to improve the delivery of medicines to the lung, a number of well known and novel generation techniques are becoming commercially available that can create relatively monodisperse nanoparticle and submicrometer aerosols without significant spray inertia effects (Gupta et al., 2003; Mazumder et al. 2006; Rabinowitz et al. 2004; Sham et al. 2004; Newth and Clark, 1989; Borgstrom et al. 2006). Submicrometer aerosols (100-1000 nm) delivered in a low inertia airstream can significantly reduce unwanted deposition in the mouth-throat region. In a recent study, Borgstrom et al. (2006) showed that reduced deposition in the highly variable MT can significantly decrease inter-subject variability in lung deposition of inhaled aerosols. However, a major problem with this delivery approach is that a high percentage of nanoparticle and submicrometer aerosols are not retained in the lungs but instead are exhaled (Heyder et al. 1986; Hofmann et al. 2001; Jaques and Kim, 2000; Morasaska et al. 1999; Morawska et al. 2005; Stahlhofen et al. 1989; Brown et al. 2002). For example, Jaques and Kim (2000) report that the total lungs retention of 100 nm aerosols can be as low as 25% without a breath hold, and Brown et al. (2002) showed that pulmonary retention of these particles is often less than 50% as these particles fail to deposit and are cleared in the exhaled air.

In order to better deliver novel pharmaceutical aerosols to the deep lung, a new generation of liquid-based drug delivery platforms is in development. These devices typically feature a decrease in initial spray or aerosol momentum, which results in a reduction in device and MT deposition. As a result of the reduced momentum approach, these delivery platforms are commonly referred to as softmist inhalers. Leading softmist inhalers were recently reviewed by Hindle (2004) and include the Respimat inhaler (Boehringer Ingelheim GmbH), the AERx inhaler (Aradigm Corp.), the Mystic inhaler (Ventaira Pharmaceuticals, Inc.), and capillary aerosol generation (CAG) (Chrysalis Technologies Inc.). Of these devices, only the Respimat inhaler is currently on the market and is only available in Europe. Clinical studies of the Respimat inhaler have indicated that a 2- to 4-fold reduction of daily doses was achieved for asthmatic patients compared with pressurized metered dose inhalers (pMDIs) (Hindle, 2004).

Computational fluid dynamic (CFD) and in vitro comparisons of a standard pMDI with the CAG system and the Respimat inhaler (Longest et al, 2008) indicated that the CAG system had relatively low and equal deposition in the inhaler mouthpiece (MP) and an attached United States Pharmacopeia (USP) standardized throat or induction port (IP), resulting in a total deposition drug loss of 20%. The Respimat inhaler had significant MP deposition (~29%) and very low IP deposition (~4%) resulting in a total deposition loss of 33%. In contrast, the pMDI resulted in 58% total deposition in the MP and IP. While these softmist systems appear to provide a significant improvement over standard pMDI technology, MT and extrathoracic deposition was still at an unacceptably high level. Thus, pulmonary deposition of pharmaceutical nanoparticles and submicrometer particles/droplets for both local and systemic therapeutics remains a challenge.

In summary, the problem to be solved is that, for inhalation therapy, very small particles (e.g. 1 μm and below) are preferable to larger particles because they pass through the mouth-throat area and into the deep lung more readily than do larger particles. However, such small particles are problematic because, once they reach the lung, their small size is not conducive to embedding (depositing) in the lung tissue, and they are frequently simply exhaled. In contrast, particles of about 4 μm or larger readily embed (deposit) in the lungs due to impaction, sedimentation, and other mechanisms (e.g. wall motion and electrostatic charge). However, large particles frequently fail to travel past the mouth-throat area and never reach the deep lung at all.

In order to make many next-generation inhaled medications a viable drug delivery alternative, the development of devices and methods for consistent targeted lung delivery and decreased inter- and intra-subject variability are of critical importance. In particular, devices and methods that deliver aerosolized submicrometer and nanometer sized particles past the mouth-throat and into the targeted areas of the respiratory tract under conditions which cause or allow the particles to embed (deposit), for example, in the deep lung, would be highly advantageous.

SUMMARY OF THE INVENTION

The invention provides devices and methods for effective delivery to the lungs of submicrometer and nanometer sized drug particles or droplets. The invention takes the following into account: 1) particles of approximately 1 μm in diameter and below have extremely low deposition rates in the mouth-throat geometry and can effectively penetrate the lungs with very little variability among patients; 2) condensational growth (water accumulation) of particles can be significant in the lungs, especially if relative humidity values in the lungs are increased above standard conditions; 3) particles on the order of 4 μm and above can effectively deposit in the deep lung; and 4) the rate and extent of particle/droplet growth can be controlled by exposure to varying temperature and relative humidity conditions. Thus, the methods and devices of the invention involve inhaling a water vapor source of controlled temperature and humidity to increase the relative humidity of the respiratory tract and the delivery of particles/droplets of approximately 1 μm or less to the increased humidity lungs. Inhalation of the water vapor can occur before, during, or after aerosol delivery. Interactions of the particles or droplets with the increased humidity field causes enhanced condensational growth of the aerosol, beyond that which would be experienced in the lungs without the inhaled water vapor. The rate and extent of particle/droplet growth and therefore the deposition site within the respiratory tract is controlled by the humidified airway conditions encountered by the particles/droplets. For example, the resulting size increase of the particles or droplets may be targeted to cause them to more efficiently deposit within deep lung regions. Deposition of the larger particles results in efficient delivery of the substances of which the particles are composed (e.g. drugs and other bioactive therapeutic agents) to the deep lung tissue, resulting in the administration of consistent, high bioavailability, known quantities of active agents with little inter- and intra-patient dosing variability.

The invention provides methods of delivering controlled amounts of one or more bioactive agents to the lungs of a subject. The method comprise the steps of: providing to the subject inhalable water vapor in an amount sufficient to cause an increase in relative humidity in the subject's respiratory tract; and providing to said subject an aerosol including particles or droplets containing said one or more bioactive agents. The increase in relative humidity is sufficient to cause the particles or droplets to increase in diameter due to water vapor condensation during passage through the subject's respiratory tract, and the increase in diameter is sufficient to cause the particles or droplets to deposit and be retained in the lungs of the subject. In one embodiment, the initial particle size is sufficiently small to cause minimal deposition in the extrathoracic region and a subsequent diameter is sufficiently large to cause enhanced deposition in the lungs. In another embodiment, an initial particle size is sufficiently small to cause minimal deposition in the extrathoracic region and a subsequent diameter is sufficiently large to cause enhanced deposition within targeted regions of the respiratory tract. "Enhanced" refers to the fact that more deposition occurs in the lungs or in a targeted region than would occur if the particle size did not increase to the larger subsequent diameter. In yet another embodiment, an initial diameter of the particles or droplets is less than 1 μm and a subsequent diameter of the particles or droplets is at least 1 μM. In further embodiments, an initial diameter of the particles or droplets is less than about 2 μm and a subsequent diameter of the particles or droplets is at least about 2 μm. For example, a subsequent diameter may be from about 2-6 μm and the particles or droplets penetrate and deposit in the deep lung. In some embodiments of the invention, the bioactive agents are, for example, peptides, proteins and nucleic acids, or pharmaceuticals and nutraceuticals. In other embodiments, the bioactive agents are, for example, environmental pollutants, bioaerosols, or chemical compounds for toxicological health effects testing. In some embodiments of the invention, both of the providing steps occur simultaneously, whereas in other embodiments, the providing steps occur sequentially. In addition, the methods may further comprise a step of heating one or both of the inhalable water vapor and the aerosol.

In other embodiments, the particles or droplets may include one or more soluble components for controlling hygroscopic or condensational growth characteristics of the particles or droplets. In other embodiments, the first providing step includes a step of providing saturated or supersaturated water vapor at a temperature of from 30° C. to 50° C. to the subject for inhalation. Further, one or more of an inhalation flow rate, a degree of supersaturation, an initial temperature, an initial particle size, an initial drug concentration, an initial degree of particle hygroscopicity, an initial aerosol number concentration, an initial total amount of inhaled water vapor, and breathing patterns may be controlled or adjusted in order to target aerosol growth and deposition within one or more specific regions of a respiratory tract. Examples of the one or more specific regions of the respiratory tract include but are not limited to an upper tracheobronchial region, a lower tracheobronchial region, and pulmonary airways.

The invention further comprises a device for delivery of one or more bioactive agents to the lungs of a subject. The device includes 1) an aerosol generation and delivery device for generating and delivering aerosol particles or droplets containing the one or more bioactive agents to the lungs of the subject, the aerosol particles or droplets having an initial diameter of 2 μm or less; and 2) a water vapor source for creating an increased relative humidity environment in the subjects's airway. The relative humidity of the increased relative humidity environment is sufficient to cause the aerosol particles or droplets to increase to a subsequent size by condensation of water vapor during passage through the subject's airway. The device may also include a control means to permit delivery of the aerosol particles or droplets after the increased relative humidity environment is attained. In some embodiments, the device includes a heating component for heating the water vapor, or the aerosol particles or droplets, or both the water vapor and the aerosol particles or droplets.

BRIEF DESCRIPTION OF THE DRAWINGS

FIG. 2A-E. Schematic illustrations of exemplary devices of the invention. A, a handheld inhaler combining a water vapor source and aerosol generator for pharmaceutical applications; Band C, device for B, inhalation of water vapor, followed by C, inhalation of aerosol, from separate containers; D, device with a switch; E, device in which water vapor and aerosol are mixed prior to inhalation.

FIGS. 3A and B. Model of the mouth-throat region and tracheobronchial tree through approximately generation G4 to G6. A, front view; B, back view.

FIGS. 8A and B. Modeled growth of albuterol sulfate droplets in the upper respiratory tract under A, subsaturated and B, supersaturated inhalation conditions.

Figure 9:
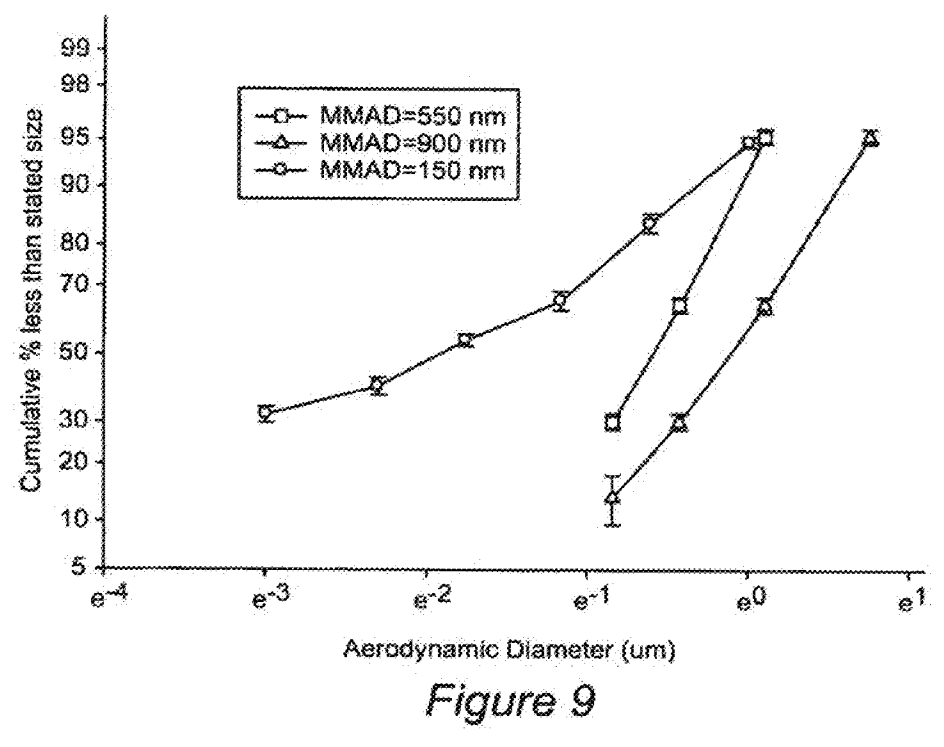

FIG. 9. Aerodynamic particle size distributions of model aerosols used for in vitro condensational growth studies.

FIG. 11. In vitro condensational growth of the 550 nm aerosol following exposure to saturated (25° C.) and supersaturated (33° C. and 43° C.) air in the tubular growth geometry.

DETAILED DESCRIPTION

Figures 1A, 1B, 1C:
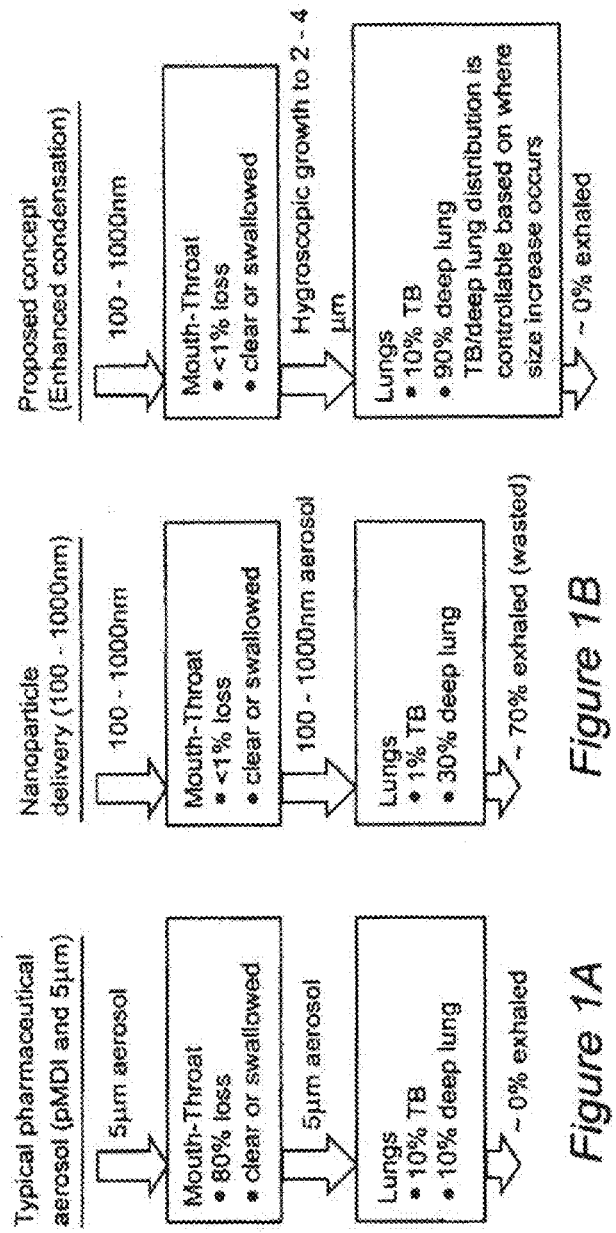
FIG. 1A-C. Comparison of particle delivery using A, conventional pharmaceutical aerosols; B, conventional nanoparticle delivery; and C, the method of the present invention.

The present invention solves an apparent contradiction in the aerosol delivery of very small particles (e.g. nanoparticles). Nanoparticles (<100 nm) and submicrometer particles (<1 μm) are preferable to larger particles for inhalation therapy because they readily pass through the mouth-throat region and into the lungs. However, because of their small size, they also tend to be exhaled rather than embedding (depositing) in the lungs. Heavier or larger particles (e.g. 4 μm or more) readily embed (deposit) in the lung tissue. However, upon inhalation, their large size (an advantage for deposition) is a disadvantage because they tend to deposit in the mouth-throat region rather than passing all the way into the lungs. Large particles thus may not reach the lung at all or may reach the lungs in an unpredictable dose. The present invention takes advantage of these two seemingly irreconcilable properties by administering nanoparticles or submicrometer particles in conjunction with a water vapor source that is at a controlled relative humidity and temperature. The inhaled water vapor is used to increase the relative humidity of the respiratory tract beyond its typical value of approximately 99.5%. In this controlled increased humidity environment, condensational growth of the nano- or submicrometer particles or droplets is enhanced converting them to larger heavier aerosols that, depending upon the rate of growth, can be targeted for deposition and retention within desired regions of the respiratory tract. In this manner, delivery of the substance(s) which makes up the particles or droplets (e.g. drugs or other therapeutic substances) is improved, and high bioavailability, uniform consistent doses are administered. This is illustrated in FIG. 1, where the characteristics of particle delivery according to the invention are shown (FIG. 1C) in comparison to those of the prior art (FIGS. 1A and 1B).

Generally, the particles or droplets that are delivered by the methods described herein are of an initial diameter in the submicrometer or nanometer range. For example, the initial size (diameter) of the particles or droplets in the aerosol prior to mixture with or prior to being exposed to high humidity conditions will generally be from about 50 nm to about 4 μm, and preferably from about 400 nm to about 1 μm. Those of skill in the art will recognize that all particles in a mixture of such particles may not be of uniform diameter, but at least about 50%, preferably about 60%, more preferably about 70%, most preferably about 80% or more (e.g. 90 or 95% or more) of the particles will have the indicated diameter. Such particles may be comprised of solid or liquid materials (e.g. solutions, emulsions, suspensions, in the form of droplets, etc.), or both (e.g. particles surrounded by or mixed with a liquid). In the latter case, the particles may be referred to as submicron- or nano-droplets. Herein, all such types of particles may be referred to as submicrometer or nanometer range (or sized) particles, submicrometer particles, nanoparticles, aerosols, particulate aerosols, droplets, etc., or even simply as "particles" for brevity.

Generally, the particles in the aerosol that is provided (administered, delivered) to the patient will increase in diameter upon exposure to or contact with a high humidity environment (e.g. with the water vapor, generally either in the lungs, or prior to that if mixing occurs prior to delivery to the patient). The particles may generally undergo a cumulative (gradual) increase in size as they travel along the route of administration, increasing from an initial diameter as described above to a subsequent (e.g. final) diameter that is large enough so they are unlikely to be exhaled. Rather, the particles become large enough to cause them to impact and embed (deposit) in the respiratory tract, thereupon releasing or delivering into the lung tissue the bioactive components that make up the particles. The particles will increase to a diameter (e.g an impacting or embedding diameter) that is typically at least greater than about 1-2 μm, preferably greater than about 3 μm, and more preferably about 4 μm or greater (e.g. the subsequent diameter may be e.g. about 5, 6, 7, 8, 9, or 10 μm). Increasing or decreasing the extent of particle growth enables targeted deposition of the particles/droplets within specific regions of the respiratory tract. Those of skill in the art will recognize that all such particles may not be of the same diameter, but at least about 50%, preferably about 60%, more preferably about 70%, most preferably about 80% or more (e.g. 90 or 95% or more) of the particles will have the indicated increased subsequent diameter.

In mammals such as humans, the relative humidity (RH) of the tracheo-bronchial airways beyond the first several bronchi is normally about 99.5%. According to the invention, either before or concomitant with delivery of particles to a subject via inhalation, water vapor (i.e. the gaseous form of water) is delivered to the lungs of a subject in order to increase the relative humidity of the subject's airways (especially the lungs) from 99.5% to an elevated humidity state that may be fully saturated (100%) or even supersaturated. That is, the relative humidity in the recipient's airways in the tracheobronchial and/or pulmonary regions (i.e. the lungs) is increased, depending on the initial and desired final particle size and preferred site of deposition to at least about 99.6%, or to at least about 99.7%, or to at least about 99.8%, or to at least about 99.9%, or even to about 100% or higher, thereby creating a controlled relative humidity environment.

By modifying the temperature and humidity of the inhaled gas phase, the relative humidity within different regions of the lungs may be controlled and increased, which can allow for targeted aerosol deposition. As one example, increasing the relative humidity in the upper tracheobronchial airways may be used to target size increase and deposition within this region. As a second example, increasing the relative humidity in the lower tracheobronchial and pulmonary airways may be used to target aerosols to deeper lung regions. Alternatively, modifying the temperature and humidity to control the rate of aerosol growth may also be used to target aerosols to specific lung regions. That is, rapid size increases can be used to target deposition in the upper tracheobronchial region whereas more gradual growth can be used to target deposition in the lower airways.

The water vapor that is delivered or administered in the practice of the invention is "breathable" or "inhalable" water vapor. By "breathable" or "inhalable" water vapor we mean that the water vapor is in a form that is physiologically compatible with and suitable for delivery to a living mammal, with respect to e.g. composition, temperature, velocity of delivery, etc. Generally, the water vapor is delivered in a carrier or medium that is a breathable, non-toxic gas (e.g. "air" or variants thereof, as described herein) that has a relative humidity that is greater than 99.5%, e.g. about 99.6%, or at least about 99.7%, or at least about 99.8%, or even at least about 99.9%, or even about 100% or higher. Again, selection of the initial relative humidity and temperature will depend on the specific region in the respiratory tract where deposition is desired. By utilizing a carrier that has a relative humidity that is at least greater than about 99.5%, the level of relative humidity in the target organ (e.g. the lungs) will be increased to above its normal level of approximately 99.5%, as described above, and particles transiting the area of increased humidity (which may be nearly saturated, saturated or supersaturated) will undergo condensational growth in size.

The relative humidity of the lungs is approximately 99.5% beyond the first several bronchi. If an inhaled aerosol contains a soluble compound, some hygroscopic size increase of the particle or droplet can occur naturally. In the proposed invention, the relative humidity of the lungs is raised above its typical value through the inhalation of a water vapor from a water vapor source. As a result, the condensation of water vapor on particles or droplets is enhanced and the related change in aerosol size is referred to as "enhanced condensational growth". Enhanced condensational growth can occur for particles or droplets containing a soluble material at relative humidity values above approximately 99.5% (assumed to be the RH in the unaltered lungs) and below 100%. Enhanced condensational growth can occur for all particles or droplets (with or without a soluble material) at relative humidity values above 100%.

The breathable, non-toxic gaseous medium or carrier which is used to deliver the water vapor to a subject may comprise the components typically found in ambient, breathable "air" (e.g. about 78% nitrogen and about 20.9% oxygen, with other trace gases such as argon). Alternatively, the water vapor may be delivered using other gaseous compositions, so long as they are not harmful to mammals. For example, gaseous medium may beneficially comprise elevated levels of oxygen, e.g. up to even about 100% $O_2$, in subjects or patients who might benefit from $O_2$ administration. Other gases such as helium, nitrous oxide, heliox, or other anesthetic gases may also be added in order to reduce turbulence, reduce airway resistance, reduce particle loss, and improve inhalation efficiency. In addition, the devices and methods of the invention may be used to administer beneficial substances together with anesthetic gases, e.g. in order to sedate a patient prior to surgery or during mechanical ventilation.

In addition, in the practice of the invention, the temperature of the water vapor and carrier medium will generally be in the range of from about 20° C. to about 48° C., and will preferably be from about 37° C. to about 43° C. Again, control of the initial temperature and relative humidity conditions can be used to target (adjust, modify, modulate, etc.) aerosol growth and deposition to specific regions of the respiratory tract, depending on the desired deposition location. The temperature may be adjusted, for example, to enable and maintain water vaporization, to store a specific amount of water in the vapor phase, to modulate condensation, to increase the comfort of the subject who will inhale the vapor (e.g. to promote compliance of self-administration), etc.

Delivery flow rates of the water vapor and the aerosol will be in the range of from about 1 to about 200 L/min, and will preferably be about 30 L/min for healthy adults. However, the invention can be designed to work at any desired flow rate. Optimal flow rates will depend on the age of the patient (including infants and the elderly) and the condition of the respiratory tract (including healthy and diseased states). This device in also proposed for veterinary applications, in which the flow rate may include the values previously stated or values outside of this range.

Various sources of inhalable, breathable water vapor or humidity will occur to those of skill in the art. For example, the Vapotherm 2000i (Stevensville, Md.) or the Humid-Heat (Gibeck, Indianapolis, Ind.) can be used to provide humidified air to a patient's airways. Likewise, various sources of aerosol nano- and/or micro-particles are known and can be employed in the practice of the invention, examples of which include but are not limited to electrospray technologies, capillary aerosol generator technology (Philip Morris USA Inc, Richmond, Va.), Staccato Inhalation Platform, (Alexza Pharmaceuticals, Mountain View, Calif.), Respimat inhaler, (Boehringer Ingelheim, Germany), and AERx inhaler (Aradigm Corp, Hayward, Calif.).

Generally, the water vapor and aerosol are delivered to the subject via the mouth or via the nose and/or mouth, and generally by voluntary breathing on the part of the subject, although this need not always be the case. In some embodiments, the subject may not be conscious or may be unable to breathe normally, or may require assistance in deep breathing, and in such cases, an assisted breathing mechanism may be used for delivery. In particular, delivery may be carried out using a mouth-piece that is inserted directly into the mouth, by using a mask that fits over the nose and mouth, intranasally, e.g. using tubes that direct the flow into the nasal passage, or even using longer tubes that deliver the flow into the throat or directly into the lungs. In addition, the increase in humidity in the lungs of the subject and delivery of the aerosol may be implemented using a tent that is saturated with the vapor. Those of skill in the art will recognize that many means exist or can be employed for delivery of water vapor and aerosol to the subject.

When voluntary breathing is employed, the subject may be instructed, for example, to take one or multiple deep breaths from a handheld version of the vapor and aerosol generator (FIG. 2A), to hold one or more of the breaths, to exhale, etc. in a prescribed manner in order to generate optimal conditions for depositing the condensationally grown particles into the lung tissue. For example, after inhaling water vapor, the subject may be instructed to exhale before inhaling the aerosol in order to clear the upper respiratory tract of excess water vapor and prevent or lessen premature condensational growth of the particles. In another variation, the patient may be instructed to take multiple breaths of a relatively high temperature saturated or supersaturated airstream in order to increase the relative humidity in the deeper lung regions.

In some embodiments of the invention, the water vapor is administered prior to administration of the aerosol, i.e. the lungs are pretreated to increase the relative humidity therein prior to administration of the aerosol. In another embodiment, in a single respiratory effort, a bolus of water vapor is inhaled over about 2 seconds followed immediately by a ~2 second inhalation of the drug aerosol. In an alternative embodiment, aerosolized particles may be mixed with the water vapor in the mouthpiece or as they exit the mouthpiece of the handheld inhaler and the two delivered together, i.e. the gaseous carrier medium that is administered to a subject will contain both water vapor and aerosolized particles. In this embodiment, the two components are mixed shortly before or immediately before administration, or within the upper respiratory tract, in order to prevent or lessen condensational growth of the particles prematurely, i.e. before they have passed through the mouth-throat region. While some growth of the particles during passage through the mouth-throat region can be tolerated, it is preferable that the particles do not exceed about 4 μm in diameter, and are more preferably smaller, e.g. 2 μm or smaller, before they enter the lungs.

The types of substances that can be administered by the methods and devices of the invention are highly varied. Generally, they will be drugs or some type of therapeutic, bioactive agent. In some embodiments, the site of action of the substance that is delivered may be the lung itself. Examples of such agents include but are not limited to agents for anesthesia; treatments for asthma or other lung conditions; anti-viral, anti-bacterial or anti-fungal agents; anti-cancer agents; α-1 antitrypsin and other antiproteases (for congenital deficiencies), rhDNAse (for cystic fibrosis), and cyclosporine (for lung transplantation), vaccines, proteins and peptides, etc. However, this need not be the case. Some agents delivered via the deep lung into systemic circulation will be distributed systemically via the circulatory system. Examples of such agents include but are not limited to, for example, calcitonin (for osteoporosis), human growth hormone (HGH, for pediatric growth deficiency), various hormones such as parathyroid hormone (PTH, for hyperparathyroidism), insulin and other protein or peptide agents, nucleic acid molecules, and anti-pain or anti-inflammation agents.

Other examples of drugs and/or active ingredient may include anti-inflammatory compounds, anti-allergics, glucocorticoids, anti-infective agents, antibiotics, antifungals, antivirals, mucolytics, antiseptics, vasoconstrictors, wound healing agents, local anaesthetics, peptides, and proteins.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, elastane, prostaglandin, leukotriene, bradykinin antagonists, non-steroidal anti-inflammatory drugs (NSAIDs), such as ibuprofen, indometacin, including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of potentially useful antiallergic agents include the afore-mentioned glucocorticoids, and nedocromil, cetrizin, loratidin, montelukast, roflumilast, ziluton, omalizumab, Heparinoids and other antihistamins, Azelastine, Cetirizin, Desloratadin, Ebastin, Fexofenadin, Levocetirizin, Loratadin.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (aziocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amidine penicillins (mecillinam); cephalosporins, including cefazolins (cefazolin, cefazedone); cefuroximes (cerufoxim, cefamdole, cefotiam), cefoxitins (cefoxitin, cefotetan, latamoxef, flomoxef), cefotaximes (cefotaxime, ceftriaxone, ceftizoxime, cefinenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole; synergists, including beta-lactamase inhibitors, such as clavulanic acid, sulbactam, and tazobactam; carbapenems, including imipenem, cilastin, meropenem, doripenem, tebipenem, ertapenem, ritipenam, and biapenem; monobactams, including aztreonam; aminoglycosides, such as apramycin, gentamicin, amikacin, isepamicin, arbekacin, tobramycin, netilmicin, spectinomycin, streptomycin, capreomycin, neomycin, paromoycin, and kanamycin; macrolides, including erythromycin, clarythromycin, roxithromycin, azithromycin, dithromycin, josamycin, spiramycin and telithromycin; gyrase inhibitors or fluoroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin; tetracyclins, including tetracyclin, oxytetracyclin, rolitetracyclin, minocyclin, doxycycline, tigecycline and aminocycline; glycopeptides, inlcuding vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin; sulfonamides, including sulfadiazine, sulfamethoxazole, sulfalene, co-trimoxazole, co-trimetrol, co-trimoxazine, and co-tetraxazine; azoles, including clotrimazole, oxiconazole, miconazole, ketoconazole, itraconazole, fluconazole, metronidazole, timidazole, bifonazol, ravuconazol, posaconazol, voriconazole, and ornidazole and other antifungals including flucytosin, griseofluvin, tonoftal, naftifin, terbinafin, amorolfin, ciclopiroxolamin, echinocandins, such as micafungin, caspofungin, anidulafungin; nitrofurans, including nitrofurantoin and nitrofuranzone; -polyenes, including amphotericin B, natamycin, nystatin, flucocytosine; other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine; antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors; plant extracts or ingredients, such as plant extracts from chamomile, hamamelis, echinacea, calendula, papain, pelargonium, essential oils, myrtol, pinen, limonen, cineole, thymol, mentol, alpha-hederin, bisabolol, lycopodin, vitapherole; wound healing compounds including dexpantenol, allantoin, vitamins, hyaluronic acid, alpha-antitrypsin, anorganic and organic zinc salts/compounds, interferones (alpha, beta, gamma), tumor necrosis factors, cytokines, interleukins.

Examples of potentially useful mucolytics are DNase, P2Y2-agonists (denufosol), heparinoids, guaifenesin, acetylcysteine, carbocysteine, ambroxol, bromhexine, lecithins, myrtol, and recombinant surfactant proteins.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil.

Examples of potentially useful peptides and proteins include antibodies against toxins produced by microorganisms, antimicrobial peptides such as cecropins, defensins, thionins, and cathelicidins.

For any of these and other explicitly mentioned examples of drug substances which are potentially useful for carrying out the invention, the compound names given herein should be understood as also referring to any pharmaceutically acceptable salts, solvates or other hydrates, prodrugs, isomers, or any other chemical or physical forms of the respective compounds comprising the respective active moieties.

Additionally drugs to treat pulmonary hypertension, such as prostacycline analogs, iloprost, remodulin, phosphodiesterase inhibitors, such as sildenafil, vardenafil, endothelian recector antagonists, such as bosentane, virustatics, including podophyllotoxine, vidarabine, tromantadine, zidovudine; ribavirin, may be added.

Also, immunmodulators including methotrexat, azathioprine, cyclosporine, tacrolimus, sirolimus, rapamycin, mofetil, cytotatics and metastasis inhibitors, alkylants, such as nimustine, melphanlane, carmustine, lomustine, cyclophosphosphamide, ifosfamide, trofosfamide, chlorambucil, busulfane, treosulfane, prednimustine, thiotepa; antimetabolites, e.g. cytarabine, fluorouracil, methotrexate, mercaptopurine, tioguanine; alkaloids, such as vinblastine, vincristine, vindesine; antibiotics, such as alcarubicine, bleomycine, dactinomycine, daunorubicine, doxorubicine, epirubicine, idarubicine, mitomycine, plicamycine; complexes of secondary group elements (e.g. Ti, Zr, V, Nb, Ta, Mo, W, Pt) such as carboplatinum, cis-platinum and metallocene compounds such as titanocendichloride; amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevacizumab, ranibizumab may be added.

Proteinase inhibitors, such as a-anti-trypsin; antioxidants, such as tocopherols, glutathion; pituitary hormones, hypothalamic hormones, regulatory peptides and their inhibiting agents, corticotropine, tetracosactide, choriogonandotropine, urofolitropine, urogonadotropine, saomatotropine, metergoline, desmopressine, oxytocine, argipressin, ornipressine, leuproreline, triptoreline, gonadoreline, buserelin, nafareline, goselerine, somatostatine; parathyroide gland hormones, calcium metabolism regulators, dihydrotachysterole, calcitonine, clodronic acid, etidronic acid; thyroid gland therapeutics; sex hormones and their inhibiting agents, anabolics, androgens, estrogens, gestagenes, antiestrogenes; anti-migraine drugs, such as proxibarbal, lisuride, methysergide, dihydroergotamine, ergotamine, clonidine, pizotifene; hypnotics, sedatives, benzodiazepines, barbiturates, cyclopyrrolones, imidazopyridines, antiepileptics, zolpidem, barbiturates, phenyloin, primidone, mesuximide, ethosuximide, sultiam, carbamazepin, valproic acid, vigabatrine; antiparkinson drugs, such as levodopa, carbidopa, benserazide, selegiline, bromocriptine, amantadine, tiapride; antiemetics, such as thiethylperazine, bromopride, domperidone, granisetrone, ondasetrone, tropisetrone, pyridoxine; analgesics, such as buprenorphine, fentanyl, morphine, codeine, hydromorphone, methadone, fenpipramide, fentanyl, piritramide, pentazocine, buprenorphine, nalbuphine, tilidine; drugs for narcosis, such as N-methylated barbiturates, thiobarbiturates, ketamine, etomidate, propofol, benzodiazepines, droperidol, haloperidol, alfentanyl, sulfentanyl; antirheumatism drugs including tumor necrosis factor-alfa, nonsteroidal antiinflammatory drugs; antidiabetic drugs, such as insulin, sulfonylurea derivatives, biguanids, glitizols, glucagon, diazoxid; cytokines, such as interleukines, interferones, tumor necrosis factor (TNF), colony stimulating factors (GM-CSF, G-CSF, M-CSF); proteins, e.g. epoetine, and peptides, e.g. parathyrin, somatomedin C; heparine, heparinoids, urokinases, streptokinases, ATP-ase, prostacycline, sexual stimulants, or genetic material may be added.

The bioactive agents that are delivered by the methods of the invention may be themselves or may comprise other ingredients that are hygroscopically active, i.e. components which tend to increase the tendency of particles to accumulate water. For example, some agents or components with which agents are typically formulated may have an intrinsic tendency to reduce the water vapor pressure on the surface of a droplet thereby accelerating the transport of water vapor to the droplet in a high humidity field. In addition, certain pharmaceuticals themselves may have a tendency to absorb water vapor to a relatively increased rate and extent. These hygroscopic compounds include but are not limited to Sodium Cromoglycate, Nedocromil Sodium, Heparin Sodium, etc. In order to attain a desired particle size in the lung, the composition of these aerosolized particles may be formulated to produce a satisfactory or optimal degree of water accumulation and particle growth. For example, the drug concentration of the aerosol may be controlled prior to exposure to the water vapor, or may be coated or mixed with various salts or other chemicals, to control the rate of water condensation and the rate of size increase.

Further, those skilled in the art will recognize that drug deposition targeting within the respiratory tract is possible by altering other parameters such as the relative humidity of the gaseous carrier, temperature and flow rate of the gaseous carrier, the initial drug aerosol particle size, drug concentration, and aerosol number density. Consider for example the concurrent delivery of an aerosol in an airstream of controlled saturated or supersaturated relative humidity and temperature. Increasing the rate and extent of aerosol size growth can be used to target deposition in the upper or mid-tracheobronchial region. Decreasing the rate and extent of aerosol size growth can be used to target deposition in the lower tracheobronchial and pulmonary regions. Modifications that will increase the rate of aerosol size growth include increasing the degree of supersaturation (e.g., from 101% to 120%), increasing the inhalation temperature (e.g. from 37° C. to 40° C., or even to 43° C.), increasing the drug concentration, incorporation of a hygroscopic formulation excipient, and decreasing the number density of particles. Modifications that will decrease the rate of aerosol size growth include decreasing the degree of supersaturation, decreasing the inhalation temperature, decreasing the drug concentration, and increasing the aerosol density. Furthermore, for a given rate of aerosol size increase, targeting the upper or lower airways can be controlled by modifying the inhalation flow rate.

Figure 2A:
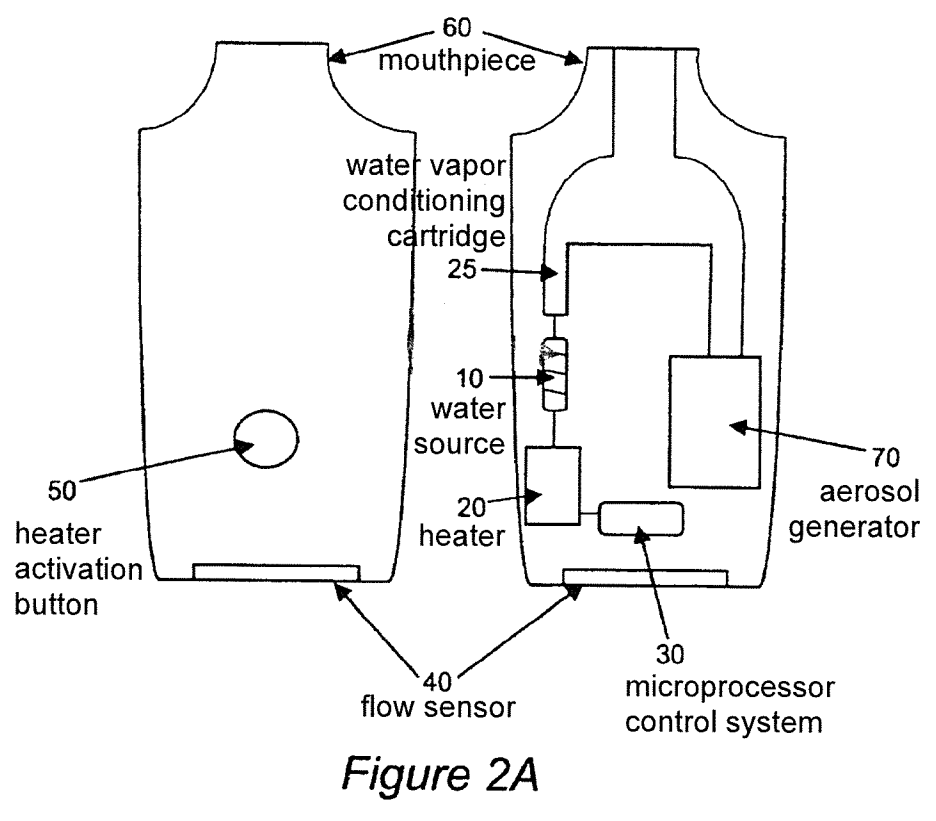

The invention also comprises devices or apparatuses for delivery of water vapor and aerosols to a patient in need thereof. A device of the invention comprises a water vapor source and submicrometer or nanoparticle aerosol generator, typically in a single handheld or tabletop portable inhaler (FIG. 2A). The inhaler provides a water source, 10 and an electrical heating means 20 to heat the water (e.g. a heating coil and battery) to create the heated water vapor. Water vapor conditioning cartridge(s) 25 may be included (Vapotherm 2000i, Stevensville, Md., or Humid-Heat; Gibeck, Indianapolis, Ind.) to condition the humidified inhalation air. Those skilled in the art would recognize that the source of the inhaled air flow could be from a miniaturized compressed air source employed within the device to deliver the water vapor to the patient or generated by the ambient air drawn into the inhaler through air flow slots and directed to the water source. A microprocessor control system 30 is provided to control the heating energy to supplied water source 10. In this embodiment, the patient prepares the inhaler by activating the heat prior to inhalation using heater activation button 50 which is connected to microprocessor control 30 and heater 20. The handheld device may be breath-actuated, in which flow sensor 40 detects the patient's inhalation and begins to release the preheated water vapor. Alternatively, the device once activated will release generated water vapor through mouthpiece 60 as it is produced. The patient inhales through mouthpiece 60 to deliver the supersaturated water vapor to the lungs. In one embodiment, the aerosol is then delivered from aerosol generator 70 (e.g. an electrospray technology or a heated capillary aerosol generator). Aerosol generation and water vapor generation is completed when the patient inhalation is completed and detected by air flow sensor 40. In this embodiment, the water vapor and drug aerosol were delivered sequentially. However, those skilled in the art will recognize that such a handheld portable inhaler may also be designed to deliver the water vapor and drug aerosol simultaneously with mixing taking place in a flow-through chamber, or within the mouthpiece as the aerosol exits the inhaler, or within the mouthpiece as the aerosol exits the inhaler, or within the patient's upper respiratory tract. A device of the invention comprises a controlled inhalable water vapor humidity source, coupled with a source of submicrometer or nanoparticulate aerosol generation and delivery.

Figure 2E:
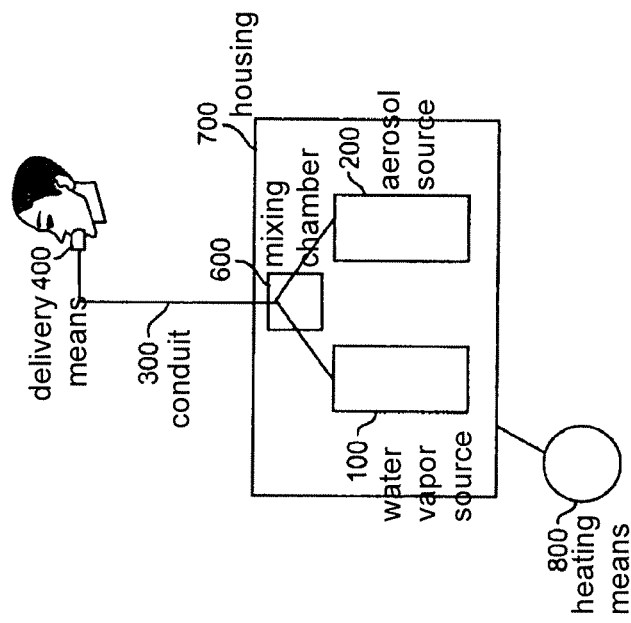
Figure 4:
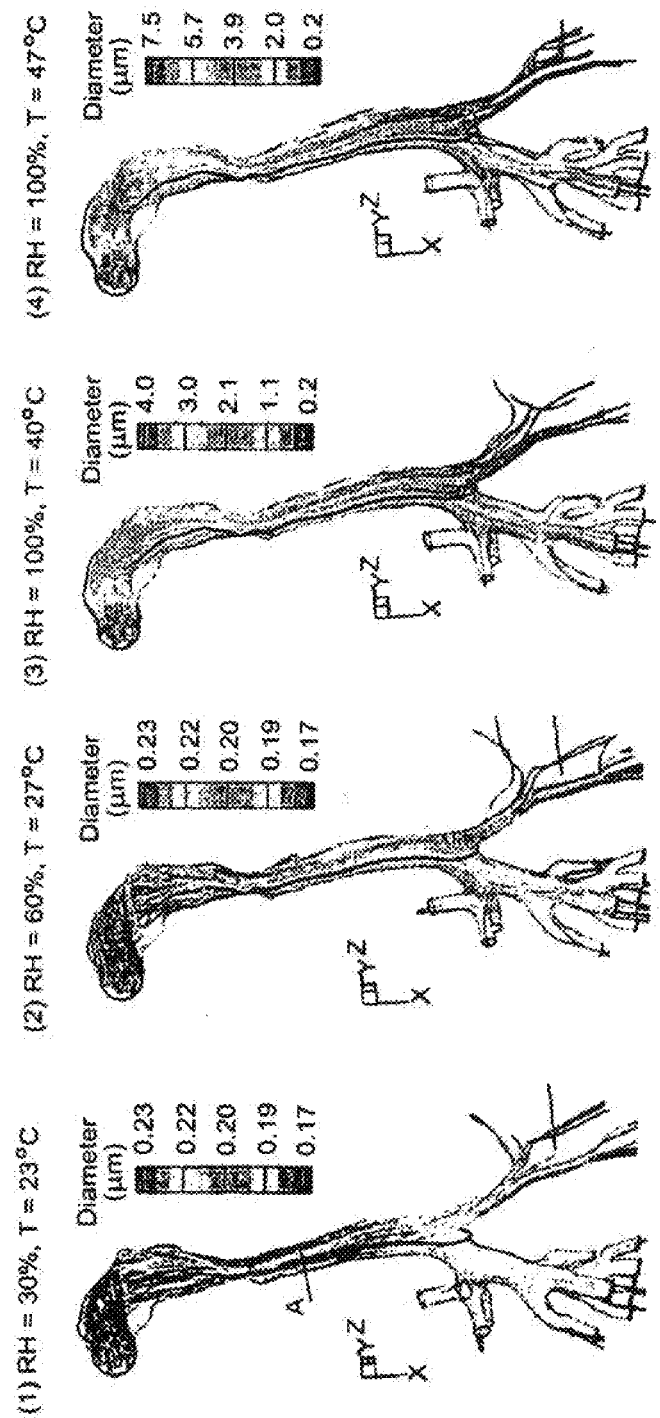
FIG. 4. Growth of initially 200 nm droplets with various relative humidity and temperature conditions. A specific humidity and temperature are inhaled at the mouth inlet and allowed to develop in the respiratory tract geometry.
Figure 5A:
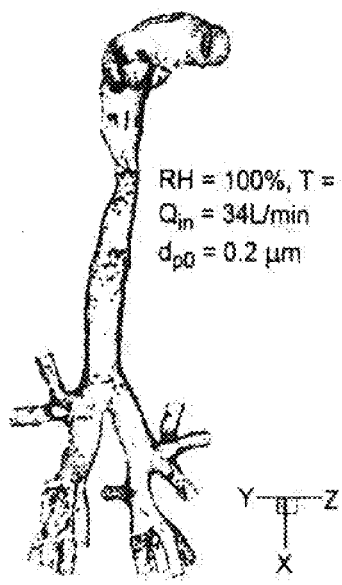
FIG. 5A-D. Comparison of localized deposition for initially 200 nm droplets with and without condensational growth. A, local deposition without growth; B, deposition enhancement factor (DEF) distribution without growth; C, local deposition with condensational growth; D, deposition enhancement factor (DEF) distribution with condensational growth. A relative humidity and temperature of RH=100% and T=40° C. were inhaled at the mouth inlet and allowed to develop in the respiratory tract geometry.
Figure 5B:
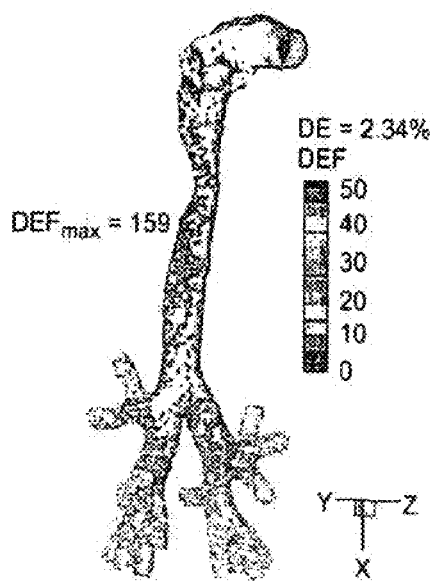
Figure 5C:
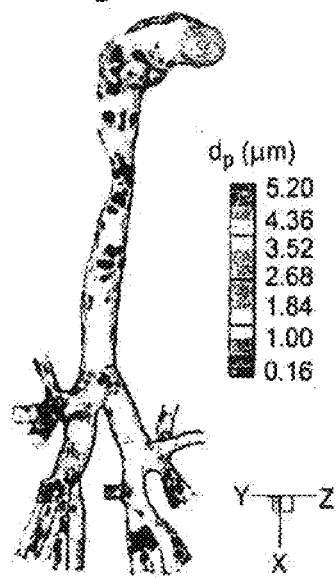
Figure 5D:
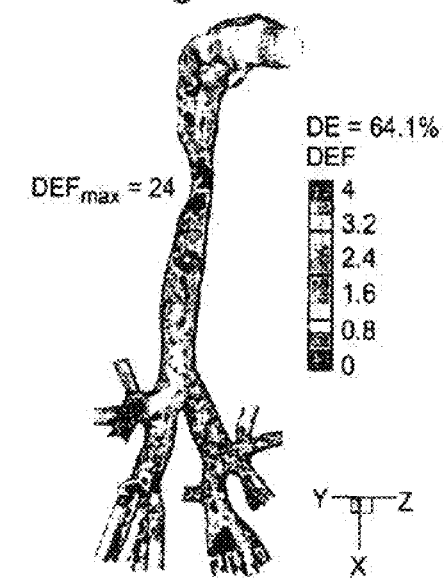

Other embodiments of devices of the invention are illustrated schematically in FIGS. 2B-E. In FIGS. 2B and 2C, water vapor source (i.e. source of humidity and temperature control) 100 and aerosol source 200 are depicted as separate devices within optional housing 700. In this embodiment, a subject first inhales saturated water vapor from water vapor source 100, the water vapor traveling through conduit 300 to a delivery means 400. Delivery means 400 may be, for example, a mouth piece, mask, tubing, etc. depending on the circumstances of use of the device. Following inhalation of water vapor sufficient to increase the relative humidity within the lungs of the subject, the subject then switches to inhalation of the aerosol from aerosol source 200. FIGS. 2B and C illustrate the case where conduit 300 is switched from one source to another. FIG. 2D illustrates an exemplary device in which control means 500 is provided to either automatically (e.g. after a prescribed period of time, or when a prescribed degree of saturation is reached, etc.) switches from water vapor source 100 to aerosol source 200. Control means 500 may represent, for example, a switch, a valve, both a valve and a switch etc. FIG. 2E schematically illustrates yet another embodiment of the device of the invention in which water vapor and aerosol are premixed in mixing chamber 600, prior to entering conduit 300 and flowing to and being inhaled by the recipient. Yet another embodiment may entail mixing of the aerosol and vapor streams within a mouthpiece or facemask, or mixing within the nasal passage, mouth-throat region, or upper tracheobronchial airways. The delivery of parallel streams of the aerosol and vapor may be used to control the rate of water uptake by the aerosol with mixing occurring, for example, as the flow moves through the larynx and enters the trachea.

Those of skill in the art will recognize that many variations in size, shape, and overall architecture of the components of the device may be utilized in order to deliver a combination of water vapor and aerosol to a subject, including various optional housings, valves, pressurizing devices, etc. In addition, heating means 800, which is a source of heat, may be included in any embodiment of the device. Generally, heating means 800 provides heat to create water vapor and/or maintain a desired water vapor temperature. Heating means 800 may also heat the aerosol. In some embodiments (e.g. when the water vapor and aerosol are delivered simultaneously) the heat source may heat both the water vapor and the aerosol, together after mixing, or separately before mixing, or both. All such configurations are intended to be encompassed by the present invention. In addition, depending on the likely scenario of use of the device, the device may be designed for single users, e.g. as relatively small (e.g. hand-held) portable refillable or disposable device for use by individuals (e.g. in the home environment); or, alternatively, as larger, non-disposable devices that may be either portable or installed for use in, for example, emergency vehicles and hospitals (e.g. at the bedside, in emergency rooms, or in operating rooms), or in other types of residential care facilities.

The subjects which are the end-users of the methods and devices of the invention are generally mammals, and are usually humans, although this need not always be the case. Veterinary applications of this technology are also contemplated. Use of this device to test the health effects of inhaled pharmaceutical aerosols or potentially toxic aerosols as a function of deposition within the lungs or a specific region of the respiratory tract is also proposed.

EXAMPLES

Example 1

To illustrate the proposed concept, an initial computational fluid dynamics (CFD) study was performed. The respiratory geometry considered was a realistic representation of the mouth-throat region (Xi and Longest, 2007) attached to a tracheobronchial model extending to respiratory generation G6 (FIG. 3). In this model, the trachea is considered to be the first respiratory generation (G1) and each downstream branch is considered a subsequent generation (i.e., G1-G6). To evaluate the effect of the relative humidity field on particle growth and deposition, four inhalation conditions were evaluated (Table 1).

TABLE 1

Inhaled relative humidity and temperature conditions at the mouth inlet

| Case | Inhaled relative humidity (RH) at the mouth (%) | Inhaled temperature (T) at the mouth (° C.) |
|---|---|---|
| 1 | 30 | 23 |
| 2 | 60 | 27 |
| 3 | 100 | 40 |
| 4 | 100 | 47 |

Figure 6A:
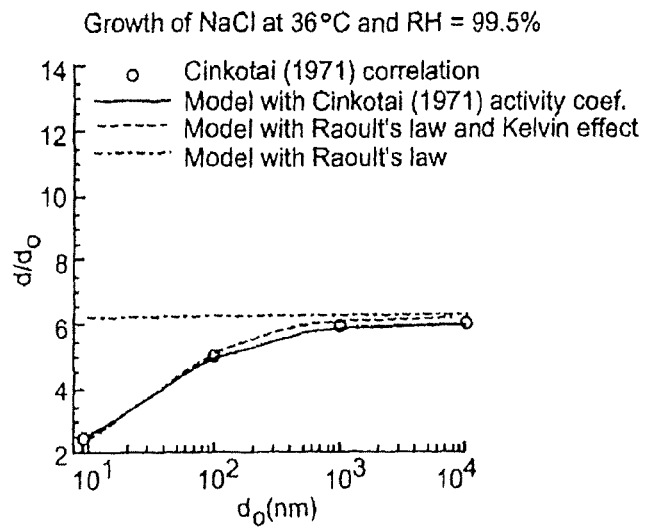
FIGS. 6A and B. Growth of NaCl aerosols from initial dry particle size ($d_o$) for RH values of (A) 99.5% and (B) 99.9%.
Figure 6B:
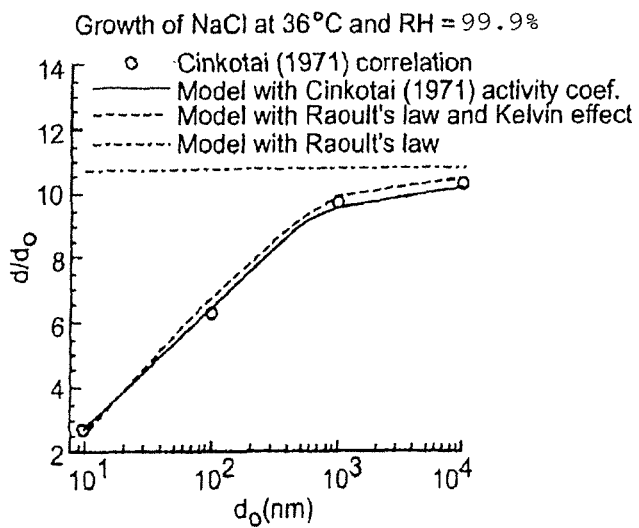

A standard medical aerosol inhalation rate of 30 L/minute was assumed and the initial particle diameter at the mouth inlet was 200 nm. The particles had no initial spray inertia. For Cases 1 and 2, a sub-saturated airstream was inhaled prior to aerosol administration. Under these conditions, some droplet evaporation was observed for inhaled aerosols in the mouth-throat region (FIG. 4). However, mass transfer from the airway walls resulted in saturated conditions and associated aerosol growth in approximately respiratory generation G6 for Case 1 and G2 for Case 2. Practically no aerosol deposition occurs for droplets with Cases 1 and 2 through the mouth-throat and tracheobronchial geometries. Cases 3 and 4 represent the inhalation of saturated water vapor. The inhalation of subsequent or concurrent aerosols is shown to result in significant particle growth for saturated conditions. Considering Case 3, very little deposition is observed in the mouth-throat region. Particles reach approximately 4 μm in diameter in the main bronchi. Enhanced deposition is observed in the conducting airways with an escalating deposition rate in more distal respiratory generations due to quick condensational growth of the aerosols (FIG. 5). Case 4 conditions result in excessive particle growth. Particles approach 6 μm before exiting the mouth-throat region. Widespread deposition then occurs in the trachea and main bronchi.

This case study illustrates the concept of controlling both aerosol growth and deposition with a prescribed relative humidity field in the lung. Considering Case 3 above, practically no deposition occurred in the mouth-throat region. As a result, little variability in mouth-throat deposition is expected. Subsequent growth in the upper bronchi of the particles to approximately 4 μm will insure significant deep lung deposition.

Example 2

Relative Humidity in the Upper Airways

To evaluate the effects of condensationAL growth on hygroscopic albuterol sulfate aerosols, realistic models of the mouth-throat (MT) and upper tracheobronchial (TB) regions were constructed based on the dimensions of an average adult male. The realistic MT geometry used in the upper airway model was originally developed by Xi and Longest (2007). This geometry was based on a dental impression cast of the mouth reported by Cheng et al. (1997) joined with a medical image-based model of the pharynx and larynx. The TB geometry used in this study was developed from a cast model of a middle aged adult male (Cohen et al., 1990). The MT and TB geometries were then smoothly connected in the region of the upper trachea (FIG. 3).

The objective of this case study was to evaluate the effects of inhaling subsaturated cool ($<T_{body}$) and saturated warm ($>T_{body}$) air on the heat and mass transport within the upper respiratory tract. The airway surfaces were assumed to be covered in a thin layer of mucus with a temperature of 37° C. and an isotonic RH=99.5%. For this preliminary case study, the inhalation flow rate was a steady 30 L/min of humidified air. The subsaturated cool inhalation condition (Case 1) was defined as $T_{inlet}$=27° C. and RH=60%. The saturated condition (Case 2) considered an inhalation that was 3° C. above body temperature ($T_{inlet}$=40° C.) with a RH=100%. A previously validated CFD model (Longest and Xi, 2007; Longest et al 2006; Longest and Vinchurkar, 2007; Longest et al., 2007) was employed to evaluate the heat and mass transfer in the respiratory tract under Case 1 and 2 inhalation conditions.

The relative humidity conditions associated with the temperature profiles for inhalation with Case 1 were $T_{inlet}$=27° C. and $RH_{inlet}$=60%. The midplane slices of the MT and TB regions showed RH profiles greater than 90% near the wall and just downstream of the main bronchi. Interestingly, RH values appear significantly lower in the right lung compared with the left. This asymmetrical result is attributed to an increased flow distribution to the right lung (60%) and the associated decrease in fluid residence time available for heat transfer from the wall.

Steady state relative humidity conditions for Case 2 were $T_{inlet}$=40° C. and $RH_{inlet}$=100%). The mid-plane slice of the MT region showed an inhaled profile of saturated air. Cooling in the MT was then observed to increase the RH to supersaturated conditions greater than 101%. This level of supersaturation was observed to persist through a major portion of the trachea. However, absorption of the supersaturated water vapor onto airway walls acted to reduce the RH values in the deeper TB region. Reduced supersaturated conditions below 101% were observed near the first carina and persisted through the main bronchi. Sub-saturated conditions with RH approaching 99.5% were not observed until the more distal bifurcations of the model.

Example 3

Condensation Growth of Single Droplets

A number of previous studies have considered the hygroscopic growth of respiratory aerosols at RH values of 100% and below. However, these studies have not addressed several questions relevant to the growth of aerosols in supersaturated respiratory environments. For example, only Ferron (1984) has briefly addressed the growth of respiratory aerosols under supersaturated conditions. Other issues include the accuracy of Raoult's law for supersaturated growth and the relevant time scales of condensation. To address these issues, a case study was conducted that considered the condensation growth of individual hygroscopic NaCl and albuterol sulfate (AS) particles and droplets. The governing equations were based on previous evaporation and condensation models for salts (Ferron, 1988), soluble and insoluble aerosols (Robinson, 1998), and multicomponent droplets (Longest, 2005). Solution of the governing equations was performed using an adaptive fourth-order Runge Kutta algorithm (Longest, 2005).

The growth ratios (final vs. initial diameter ($d_o$) for pure NaCl particles under RH conditions of 99.5 and 99.9% are shown in FIGS. 6A-B. Predictions of the numerical model were compared with the empirical correlation of Cinkotai (1971), which was based on experimental observations for initially pure NaCl particles under a range of RH conditions.

Three models were considered to evaluate the hygroscopic properties of the NaCl droplets. These models were (1) a concentration dependent activity coefficient, (2) Raoult's law with Kelvin and Fuch's corrections, and (3) only Raoult's law. Considering a RH of 99.5%, the concentration dependent activity coefficient model matched the empirical size change data to a high degree (FIG. 6A). Similarly, Raoult's law with Kelvin and Fuch's effects appears to provide good agreement with the experimental data. In contrast, Raoult's law alone over-predicts condensation growth in the submicrometer range, as expected. Increasing the RH from 99.5 to 99.9% (FIG. 6A vs. 6B), is observed to increase the condensation growth ratio by a factor of two. As a result, NaCl particles in the range of 100-1000 nm are observed to increase in size by a growth factor of 6-10 at a RH of 99.9%.

Figure 7A:
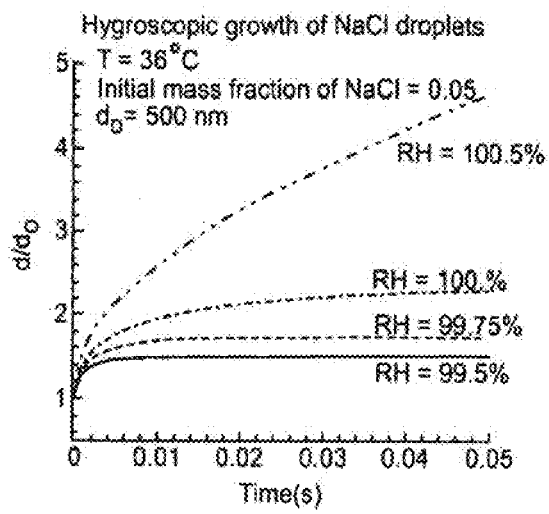
FIGS. 7A and B. Size change over time at different RH conditions for (A) NaCl and (B) albuterol sulfate (AS) droplets.
Figure 7B:
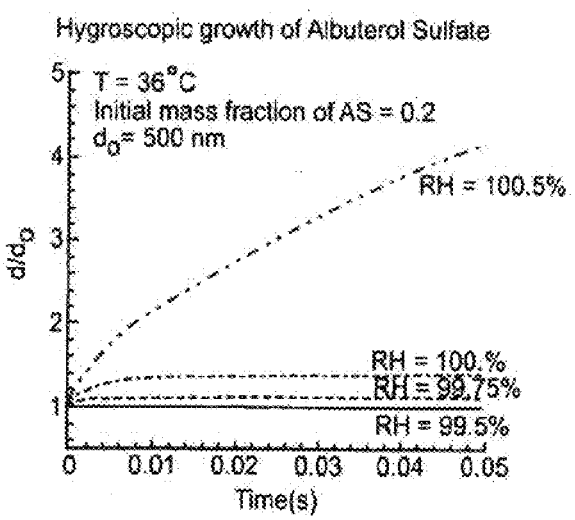

The condensation growth ratios of hygroscopic NaCl and AS droplets are compared in FIG. 7A-B for various RH values. NaCl is considered as a model salt that may be mixed with drug constituents to modify the hygroscopic nature of a particle or droplet. The initial droplet diameter was 500 nm and the surrounding flow field was at 36° C. For subsaturated conditions, both NaCl and AS aerosols quickly reach an equilibrium size, which is a function of the initial concentration and hygroscopic properties of the solute (FIG. 7). Under supersaturated conditions, equilibrium is not reached and condensation continues to occur. At a RH of 100.5%, the NaCl and AS droplets both increase in size by a factor of approximately 4 within 0.05 s.

Based on these results, a single hygroscopic particle or droplet can increase in size by a significant amount in the respiratory tract. However, the amount of vapor present in the gas phase may limit the amount of growth that is possible for aerosols in a dense cloud. An aerosol-vapor system that is influenced by the amount of available vapor is termed "two-way coupled". That is, the condensation of vapor affects both the droplet mass and the remaining vapor concentration. Finlay (1998) has conducted an analytical non-dimensional analysis of condensation growth to predict (1) if hygroscopic size increase occurs and (2) if coupled effects are important. Finlay (1998) defined $\xi$ as the ratio of added droplet mass to existing droplet mass, which is large if the size change is significant. The second parameter, $\gamma$, represents the ratio of particle mass to the available mass for condensation until equilibrium is reached. A small value of $\gamma$ indicates one-way coupling.

The non-dimensional parameters suggested by Finlay are reported in Table 1 for a 500 nm droplet with 20% AS and surrounding conditions of RH=101% and 37° C. Based on the large value of $\xi$ the potential for condensation growth appears significant. For standard nebulizers, particle concentration can vary from approximately $1\times10^4$-$1\times10^6$. At the lower end of this range, $\gamma$ values indicate that condensation growth can be one- or two-way coupled (Table 1). For higher aerosol concentrations, the condensation is clearly two-way coupled and may be significantly limited. This analysis indicates that condensation growth may be highly effective in the rage of $1\times10^3$-$1\times10^4$ particles/cm$^3$. Two way coupling effects will likely be significant for higher aerosol concentrations. As a result, RH values above 101% may be needed to provide sufficient vapor mass at high aerosol concentrations.

TABLE 2

Effects of aerosol concentration on condensation growth.

| Particle concentration (particles/cm$^3$) | Particle mass per unit volume $\epsilon$ (g/cm$^3$) | Available(2) mass of water vapor $\Delta c^*$ (g/cm$^3$) | $\xi$ | $\gamma$ | Coupling |
|---|---|---|---|---|---|
| $1 \times 10^3$ | $6.54 \times 10^{-5}$ | $4.1 \times 10^{-6}$ | 5668 | 0.16 | One way |
| $1 \times 10^4$(1) | $6.54 \times 10^{-6}$ | $4.1 \times 10^{-6}$ | 5668 | 1.6 | One or two way |
| $1 \times 10^5$(1) | $6.54 \times 10^{-7}$ | $4.1 \times 10^{-6}$ | 5668 | 1.6 | Two way |
| $1 \times 10^6$(1) | $6.54 \times 10^{-8}$ | $4.1 \times 10^{-6}$ | 5668 | 16 | Two way |

The conditions in the table below are for an initially 500 nm droplet with a mass fraction of 20% albuterol sulfate and surrounding conditions of T = 37° C. and RH = 101%.
(1)Particle number concentration of common nebulizers (Finlay 1998)
(2)Mass of water vapor available for transfer until equilibrium with the droplet surface is reached.

Example 4

Condensation Growth in the Respiratory Tract

Computational fluid dynamics (CFD) predictions of condensation aerosol growth in a model of the upper respiratory tract are shown in FIG. 8. Both subsaturated (FIG. 8A) and supersaturated (FIG. 8B) inhalation conditions were considered. The aerosol was initially dilute 200 nm liquid droplets of AS (mass fraction=20%) in water. For the subsaturated airway conditions, the AS droplets are observed to initially evaporate in the upper respiratory tract. However, some condensation growth was observed in the lower branches as the RH approached 99.5% (FIG. 8). For the supersaturated case, significant growth was observed throughout the geometry. The initially 200 nm particles are observed to reach a size of approximately 2 µm in the trachea. An aerosol of approximately 4 µm was achieved at the model outlets. As a result, low deposition is expected in the MT region. In contrast, aerosol deposition consistent with a standard inhaled micrometer aerosol is expected in the TB and lower respiratory tract.

Example 5

Enhanced Lung Delivery of Nano- and Micro-Sized Pharmaceutical Aerosols

In this example, condensational growth in a tubular geometry of 25 cm (approximate length from mouth inlet to first bifurcation) was investigated experimentally. The in vitro setup consisted of aerosol and supersaturated humidity generators, a tubular geometry for aerosol growth, a flow control system, and aerosol sampling and sizing components. Aqueous-based droplet aerosols were generated in the submicrometer range (100 nm<$d_p$<1000 nm) using a small particle aerosol generator (SPAG-6000, ICN Pharmaceuticals, Costa Mesa, Calif.). Albuterol sulfate (model drug) solutions were nebulized using a series of nebulizer airflow conditions to produce aerosols with mean (SD) measured sizes of 150 (10)

nm, 550 (10) nm and 900 (30) nm, respectively (FIG. 9). The 150 nm aerosol was generated using a 0.1% albuterol sulfate in water solution nebulized with a nebulizer gas flow rate of 7.5 L/min and a drying gas flow rate of 9 L/min. The 550 nm aerosol was generated using a 0.1% albuterol sulfate in water solution nebulized with a nebulizer gas flow rate of 7.5 L/min and a drying gas flow rate of 3 L/min. The 900 nm aerosol was generated using a 0.5% albuterol sulfate in water solution nebulized with a nebulizer gas flow rate of 7.5 L/min and a drying gas flow rate of 3 L/min. A modified compressed air-driven humidifier system (Vapotherm 2000i, Stevensville, Md.) was employed to generate heated saturated and supersaturated air conditions flowing through the tubular geometry. In this example, saturated air at 25° C., together with supersaturated air at 33° C. and 43° C. was used. Other temperatures may be preferred depending upon the required aerosol growth. Appropriate temperature and relative humidity measurements were made using the Vaisala HUMICAP Handheld Meter (HM70, Helsinki, Finland). Aerosol particle concentration was monitored using a condensation particle counter (TSI 3022A, Shoreview, Minn.). In this example, final aerosol drug size was measured in the Andersen Cascade Impactor, operated at 28 L/min in an ESPEC environmental chamber maintained at 37° C. and >95% RH.

Figure 10:
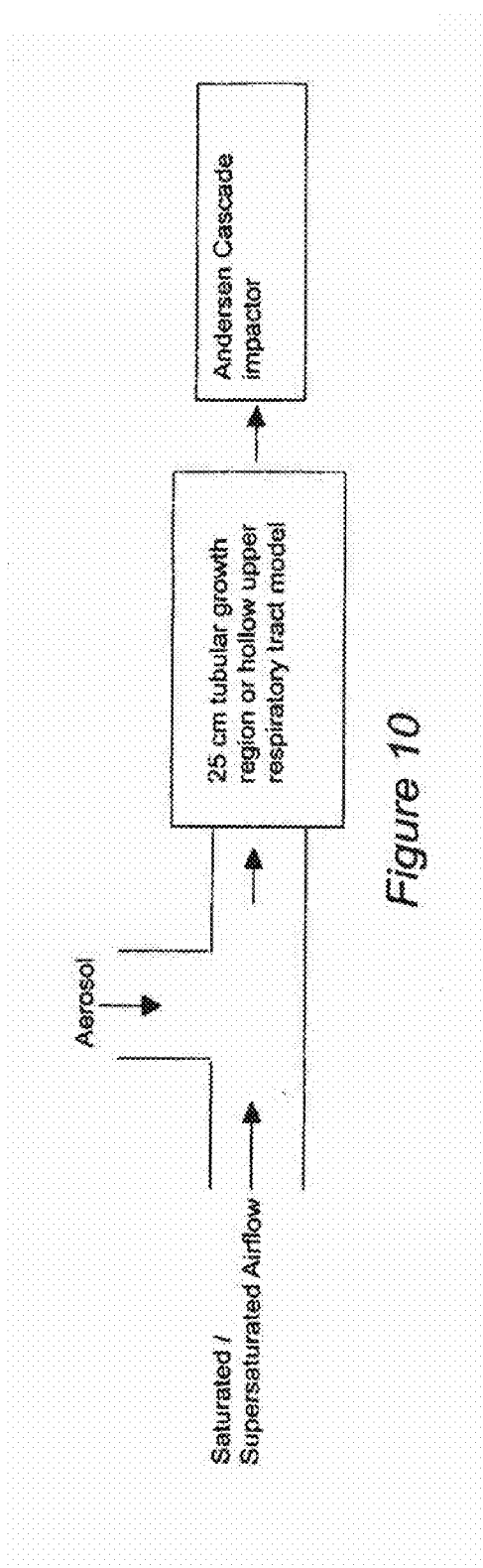
FIG. 10. Schematic representation of the in vitro experimental setup for Example 5.

FIG. 10 shows a schematic representation of the experimental setup used in this study. In this example, the saturated or supersaturated air was mixed with the model aerosol using a 90 degree mixing tee junction. Other mixing orientations may be preferred depending upon the required aerosol growth characteristics.

FIG. 11 shows the condensational growth of the 550 nm model aerosol following exposure to saturated air at 25° C. and supersaturated air at 33° C. and 43° C., respectively, after transit through the tubular geometry. The Mass Median Aerodynamic Diameter (MMAD) of the aerosol represents the 50th percentile on a cumulative frequency versus aerodynamic diameter plot. Aerosol concentration was measured at the entrance to the Andersen cascade impactor. In this example, the total nebulizer air flow rate was 10.5 L/min and the saturated/supersaturated air flow was 20 L/min. There was significant condensation growth observed for both the 33° C. and 43° C. air flow conditions, compared to the saturated air flow at 25° C. Those skilled in the art will recognize that variation in the saturated/supersaturated air flow rates and temperatures, together with the mixing conditions during the introduction of the drug aerosol and drug aerosol concentration, will each produce changes in the degree of condensational growth. Optimization of these parameters enable selective targeting of nano-sized aerosol particles to be delivered and retained in different regions of the respiratory tract.

Table 3 shows the mean (SD) MMAD for the three test aerosols with initial sizes of 150, 550 and 900 nm following exposure to saturated (25° C.) and supersaturated (33° C. and 43° C.) air in the tubular growth geometry. In each of the examples, submicrometer aerosols were observed to have significant condensational growth when exposed to supersaturated airflow conditions (33° C. and 43° C.) in the model geometry compared to the aerosols exposed to saturated airflow at 25° C. under identical conditions. The mean growth ratios compared to the initial measured MMAD for the 150 nm aerosol at 33° C. and 43° C. were 7.2 and 8.5, respectively. Similar values for the 550 nm aerosol were 3.8 and 4.8. The growth ratios for the 900 nm aerosol were 1.1 and 2.8. The initial submicrometer aerosol size considered in this example is ideal for passing through the mouth-throat region without depositional losses. The final size in the range of 3 μm is ideal for deep lung penetration and deposition. These initial studies indicate the feasibility of condensational growth of pharmaceutical aerosols using a range of initial drug aerosol concentrations and droplet particle sizes.

TABLE 3

Mean (SD) MMAD for three model albuterol aerosols exposed to saturated and supersaturated air.

| Initial Size | Mass Median Aerodynamic Diameter (MMAD) | | |
|---|---|---|---|
| | 25° C. | 33° C. | 43° C. |
| 150 nm* | 0.51 μm (0.04) | 1.08 μm (0.02) | 1.27 μm (0.23) |
| 550 nm | 0.64 μm (0.01) | 2.10 μm (0.27) | 2.68 μm (0.35) |
| 900 nm | 0.82 μm (0.08) | 0.98 μm (0.04) | 2.50 μm (0.24) |

*Saturated and supersaturated air flow was 25 L/min in this example

Example 6

Figure 12B:
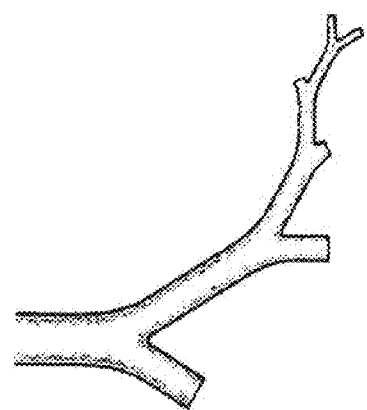
FIGS. 12A and B. Schematic drawing of A, the mouth-throat and B, model segment of the upper tracheobronchial airways.
Figure 12A:
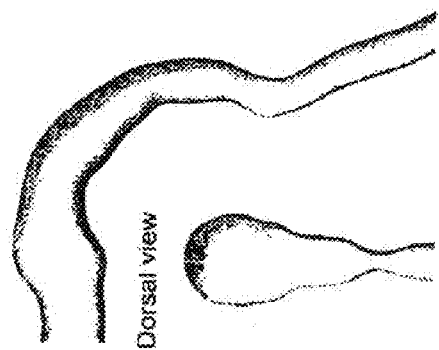

In this example, aerosol drug transport and deposition was evaluated in a hollow replica model of the upper respiratory tract based on experimental analysis. A representative physical hollow model of the upper respiratory tract was constructed with in-house rapid prototyping capabilities on a Viper SLA system (3D Systems, Valencia, Calif.). This respiratory tract model consisted of an idealized elliptical mouth-throat geometry coupled with a representative model of airway generations from the trachea (G0) through G5 (FIG. 12). The in vitro setup consisted of aerosol and supersaturated humidity generators, a geometric model of the upper respiratory tract, a flow control system, and aerosol sampling and sizing components. Aqueous-based droplet aerosols were generated in the submicrometer regime (100 nm<$d_p$<1000 nm) using a small particle aerosol generator (SPAG-6000, ICN Pharmaceuticals, Costa Mesa, Calif.). Albuterol sulfate (model drug) solutions were nebulized using a series of nebulizer airflow conditions to produce aerosols with mean (SD) measured sizes of 150 (10) nm, 550 (10) nm and 900 (30) nm, respectively. The 150 nm aerosol was generated using a 0.1% albuterol sulfate in water solution nebulized with a nebulizer gas flow rate of 7.5 L/min and a drying gas flow rate of 9 L/min. The 550 nm aerosol was generated using a 0.1% albuterol sulfate in water solution nebulized with a nebulizer gas flow rate of 7.5 L/min and a drying gas flow rate of 3 L/min. The 900 nm aerosol was generated using a 0.5% albuterol sulfate in water solution nebulized with a nebulizer gas flow rate of 7 L/min and a drying gas flow rate of 3 L/min. A modified compressed air-driven humidifier system (Vapotherm 2000i, Stevensville, Md.) was employed to generate heated saturated and supersaturated air conditions flowing through the tubular geometry. In this example, saturated air at 25° C. and supersaturated air at 43° C. was used. Other temperatures may be preferred depending upon the required aerosol growth. Appropriate temperature and relative humidity measurements were made using the Vaisala HUMICAP Handheld Meter (HM70, Helsinki, Finland). Aerosol particle concentration was monitored using a condensation particle counter (TSI 3022A, Shoreview, Minn.). In this example, aerosol drug deposition in the model of the upper respiratory tract was determined using quantitative HPLC analysis of washings from the airway model. The airway model was placed in an ESPEC environmental chamber maintained at 37° C. and >95% RH for each study. To facilitate uniform flow control in the in vitro geometry, needle valve flow controllers and rotameters were connected by tubing to each outlet and adjusted to provide appropriately divided mass flow at each bifurcation. FIG. 10 shows a schematic representation of the experimental setup used in this study. In this example, the saturated or supersaturated air was mixed with the model aerosol using a 90 degree mixing tee junction. Other mixing orientations may be preferred depending upon the required aerosol growth.

The mean (SD) albuterol aerosol drug deposition in the upper respiratory hollow model is shown in Table 4. In this example, aerosol and saturated or supersaturated air is delivered immediately into the hollow airway model. Therefore, in this model, condensation growth takes place as the aerosol is flowing through the airway model.

TABLE 4

Mean (SD) albuterol drug deposition on the upper respiratory tract model.

| Initial | | % albuterol drug deposition in airway model | |
|---|---|---|---|
| Size | Aerosol concentration | 25° C. | 43° C. |
| 150 nm | $9.3 \times 10^4$ particles/cm$^3$ | 0.8% (0.3) | 1.5% (0.4) |
| 550 nm | $1.4 \times 10^5$ particles/cm$^3$ | 2.1% (1.1) | 8.0% (1.6) |
| 900 nm | $2.3 \times 10^5$ particles/cm$^3$ | 8.2% (0.9) | 14.8% (1.3) |

As can be seen, the 150 nm aerosol showed minimal deposition in the upper respiratory tract model following inhalation with saturated air at 25° C. There was an 87% increase in drug deposition when exposed to supersaturated air at 43° C. Low levels of drug deposition would be expected given the initial aerosol size and the expected growth observed in Example 5 (150 nm aerosol at 43° C.=1.27 µm). These conditions may be favorable when peripheral lung deposition is required.

The 550 nm aerosol showed a significantly increased drug deposition in the upper respiratory tract model following inhalation with 43° C. supersaturated air compared to saturated air at 25° C. The deposition increased from 2.1% to 8.0% indicating the enhanced condensational growth taking place as the aerosol is transported through the airway model. A similar change was observed with the 900 nm aerosol.

REFERENCES

Borgstrom L, Olsson B and Thorsson L. Degree of throat deposition can explain the variability in lung deposition of inhaled drugs. Journal of Aerosol Medicine 2006; 19:473-483.
Byron P R. Drug delivery devices: Issues in drug development. Proc. Am. Thorac. Soc. 2004; 1:321-328.
Cinkotai F F. The behavior of sodium chloride particles in moist air. Journal of Aerosol Science 1971; 2:325-329.
Dalby, R., Spallek, M, and Voshnaar, T. (2004) A review of the development of Respimat soft mist inhaler, International Journal of Pharmaceutics 283: 1-9.
Ferron G A, Haider B and Kreyling W G. Conditions for measuring supersaturation in the human lung using aerosols. Journal of Aerosol Science 1984; 15:211-215.
Ferron G A, Kreyling W G and Haider B. Inhalation of salt aerosol particles-II. Growth and deposition in the human respiratory tract. Journal of Aerosol Science 1988; 19:611-631.
Finlay W H. Estimating the type of hygroscopic behavior exhibited by aqueous droplets. Journal of Aerosol Medicine 1998; 11:221-229.
Gupta R, Hindle M, Byron P R, Cox K A and McRae D D. Investigation of a novel condensation aerosol generator: Solute and solvent effects. Aerosol Science and Technology 2003; 37:672-681.
Hindle M, Gupta R and Cox K A. Adding pharmaceutical flexibility to the capillary aerosol generator. In Respiratory Drug Delivery IX (Dalby, R N, Byron, P R, Peart, J, Suman, J D and Farr, S J, eds.), pp. 247-254, DHI Publishing, River Grove, Ill., 2004.
Heyder J, Gebhart J, Rudolf G, Schiller C F and Stahlhofen W. Deposition of particles in the human respiratory tract in the size range of 0.005-15 microns. Journal of Aerosol Science 1986; 17:811-825.
Hofmann W, Morawska L and Bergmann R. Environmental tobacco smoke deposition in the human respiratory tract: differences between experimental and theoretical approaches. Journal of Aerosol Medicine 2001; 14:317-326.
Jaques P A and Kim C S. Measurement of total lung deposition of inhaled ultrafine particles in healthy men and women. Inhalation Toxicology 2000; 12:715-731.
Longest P W and Kleinstreuer C. Computational models for simulating multicomponent aerosol evaporation in the upper respiratory airways. Aerosol Science and Technology 2005; 39:124-138.
Longest P W and Oldham M J. Mutual enhancements of CFD modeling and experimental data: A case study of one micrometer particle deposition in a branching airway model. Inhalation Toxicology 2006; 18:761-772.
Longest P W, Hindle M, Das Choudhuri S and Byron P R. Numerical simulations of capillary aerosol generation: CFD model development and comparisons with experimental data. Aerosol Science and Technology 2007; 41:952-973.
Longest P W and Vinchurkar S. Effects of mesh style and grid convergence on particle deposition in bifurcating airway models with comparisons to experimental data. Medical Engineering and Physics 2007; 29:350-366.
Longest P W and Xi J. Effectiveness of direct Lagrangian tracking models for simulating nanoparticle deposition in the upper airways. Aerosol Science and Technology 2007; 41:380-397.
Longest P W, Hindle M, Das Choudhuri S and Byron P R. Developing a better understanding of spray system design using a combination of CFD modeling and experiment. In Respiratory Drug Delivery 2008 (Dalby, R N, Byron, P R and Peart, J, eds.), in press 2008.
Martonen, T. B. (1993) Mathematical-Model for the selective Deposition of Inhaled Pharmaceuticals, Journal of Pharmaceutical Sciences 82(12): 1191-1199.
Mazumder M K, Sims R A, Biris A S, Srirama P K, Saini D, Yurteri C U, Trigwell S, S. D and Sharma R. Twenty-first century research needs in electrostatic processes applied to industry and medicine. Chemical Engineering Science 2006; 61:2192-2211.
Morawska L, Barron W and Hitchins J. Experimental deposition of environmental tobacco smoke submicrometer particulate matter in the human respiratory tract. American Industrial Hygiene Association Journal 1999; 60:334-339.
Morawska L, Hofmann W, Hitchins-Loveday J, Swanson C and Mengersen K. Experimental study of the deposition of combustion aerosols in the human respiratory tract. Journal of Aerosol Science 2005; 36:939-957.
Rabinowitz J D, Wensley M, Lloyd P, Myers D, Shen W, Lu A, Hodges C, Hale R, Mufson D and Zaffaroni A. Fast onset medications through thermally generated aerosols. The Journal of Pharmacology and Experimental Therapeutics 2004; 309:769-775.
Robinson R and Yu C P. Theoretical analysis of hygroscopic growth rate of mainstream and sidestream cigarette smoke particles in the human respiratory tract. Aerosol Science and Technology 1998; 28:21-32.

Sham JO-H, Zhang Y, Finlay W H, Roa W H and Lobenberg R. Formulation and characterization of spray-dried powders containing nanoparticles for aerosol delivery to the lung. International Journal of Pharmaceutics 2004; 269: 457-467.

Newth C J L and Clark A. In vitro performance of the small particle aerosol generator (SPAG-2). Pediatric Pulmonology 1989; 7:183-188.

Smaldone, G. C. (2006) Advances in aerosols: Adult resporiatory disease, Journal of Aerosol Medicine 19(1): 36-46.

Stahlhofen W, Rudolf G and James A C. Intercomparison of experimental regional aerosol deposition data. Journal of Aerosol Medicine 1989; 2:285-308.

Xi J and Longest P W. Transport and deposition of microaerosols in realistic and simplified models of the oral airway. Annals of Biomedical Engineering 2007; 35:560-581.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of delivering controlled amounts of one or more bioactive agents to the lungs of a subject, comprising the steps of:
   providing to said subject inhalable water vapor in a first stream;
   providing to said subject an aerosol including particles or droplets containing said one or more bioactive agents in a second stream, said particles or droplets having an initial diameter of 2 µm or less to minimize deposition of said particles or droplets in the mouth and throat of said subject; and
   mixing said first stream and said second stream in one or more of a mixing device, the nasal passage, the mouth-throat region, and the upper tracheobronchial airways of said subject;
   wherein said step of providing inhalable water vapor creates supersaturated relative humidity in said subject's respiratory tract;
   wherein said particles or droplets are caused by said supersaturated relative humidity to increase in diameter in said subject's respiratory tract due to water vapor condensation; and
   wherein a subsequent diameter of said particles or droplets in said subject's respiratory tract causes enhanced deposition in the lungs.

2. The method of claim 1, wherein said inhalable water vapor has a temperature at 37° C. or above.

3. The method of claim 1, wherein an initial diameter of said particles or droplets provided in said providing step is less than 1 µm.

4. The method of claim 1, wherein said subsequent diameter of said particles or droplets after said mixing step is increased to 2-6 µm.

5. The method of claim 1 wherein said bioactive agents are selected from peptides, proteins and nucleic acids.

6. The method of claim 1 wherein said bioactive agents are selected from pharmaceuticals and nutraceuticals.

7. The method of claim 1 wherein said bioactive agents are selected from environmental pollutants, bioaerosols, or chemical compounds for toxicological health effects testing.

8. The method of claim 1 further comprising a step of heating one or both of said inhalable water vapor and said aerosol.

9. The method of claim 1 wherein said particles or droplets include one or more soluble components for controlling hygroscopic or condensational growth characteristics of said particles or droplets.

10. The method of claim 1 wherein said inhalable water vapor has a temperature of from 30° C. to 50° C.

11. The method of claim 1 wherein one or more of an inhalation flow rate, a degree of supersaturation, an initial temperature, an initial particle size, an initial drug concentration, an initial degree of particle hygroscopicity, an initial aerosol number concentration, an initial total amount of inhaled water vapor, and breathing patterns are controlled in order to target aerosol growth and deposition within one or more specific regions of a respiratory tract.

12. The method of claim 11, wherein said one or more specific regions of said respiratory tract include an upper tracheobronchial region, a lower tracheobronchial region, and pulmonary airways.

13. The method of claim 1, wherein said mixing device of said mixing step is selected from a flow-through chamber, a mouthpiece, a facemask, a mixing tee junction, an assisted breathing mechanism, a tent, and a device configured for delivery of parallel streams of said water vapor and said aerosol into one or more of
   the mouth,
   the nasal passage,
   the mouth-throat region, and
   the upper tracheobronchial airways of said subject.

14. The method of claim 1, wherein said subsequent diameter of said particles or droplets after said mixing step does not exceed 4 µm prior to entering the lungs.

15. A device for delivery of one or more bioactive agents to the lungs of a subject, comprising:
   a water vapor source for delivering inhalable water vapor in a first stream,
   an aerosol generation and delivery device for generating and delivering aerosol particles or droplets containing said one or more bioactive agents in a second stream, said particles or droplets having an initial diameter of 2 µm or less to minimize deposition of said particles or droplets in the mouth and throat of said subject, and
   a mixing device configured for mixing said first stream and said second stream, said mixing device being selected from a flow-through chamber, a mouthpiece, a facemask, a mixing tee junction, an assisted breathing mechanism, and a tent;
   wherein said inhalable water vapor creates supersaturated relative humidity in said subject's respiratory tract;
   wherein said particles or droplets are caused by said supersaturated relative humidity to increase in diameter in said subject's respiratory tract due to water vapor condensation; and
   wherein a subsequent diameter of said particles or droplets in said subject's respiratory tract causes enhanced deposition in the lungs.

16. The device of claim 15, further comprising a heating component for heating said water vapor, or said aerosol particles or droplets, or both said water vapor and said aerosol particles or droplets.

17. The device of claim 15, further comprising a controller for controlling said water vapor source.

* * * * *